United States Patent [19]

Kitayama

[11] Patent Number: 5,189,890
[45] Date of Patent: Mar. 2, 1993

[54] PORTABLE CHILLER
[75] Inventor: Daisuke Kitayama, Osaka, Japan
[73] Assignee: Senju Seiyaku Kabushiki Kaisha, Osaka, Japan
[21] Appl. No.: 914,656
[22] Filed: Jul. 17, 1992

Related U.S. Application Data

[63] Continuation of Ser. No. 705,672, May 24, 1991, abandoned.

[30] Foreign Application Priority Data

Jun. 1, 1990 [JP]  Japan .................................. 2-145046
Jun. 14, 1990 [JP] Japan .................................. 2-156714

[51] Int. Cl.$^5$ ............................................... F25D 3/08
[52] U.S. Cl. ........................................ 62/293; 62/371; 62/457.9
[58] Field of Search .............. 62/457.2, 457.4, 457.9, 62/315, 316, 293, 371

[56] References Cited

U.S. PATENT DOCUMENTS

| | | | |
|---|---|---|---|
| 2,775,872 | 1/1957 | Bell | 62/457.2 X |
| 2,805,556 | 9/1957 | Wang | 62/457.4 X |
| 3,529,437 | 9/1970 | Bell | 62/315 X |
| 4,054,037 | 10/1977 | Yoder | 62/457.9 X |
| 4,640,101 | 2/1987 | Johnson | 62/457.9 X |

Primary Examiner—William E. Tapolcai
Attorney, Agent, or Firm—Armstrong, Westerman, Hattori, McLeland & Naughton

[57] ABSTRACT

Here is described a portable chiller with which an ophthalmic solution, cosmetic preparation, beverage or the like in a small container can be conveniently chilled. This portable chiller consists generally of a cylinder filled with a liquefied refrigerant gas and a chiller case. This chiller case includes a cylinderloading compartment, a cooling compartment in which the article is chilled, and a refrigerant ejection device for ejecting the refrigerant from the cylinder accommodated in the cylinder compartment into the cooling compartment. Disposed in the cooling compartment is a device adapted to keep a vent orifice of the cooling compartment to withhold gasification of the refrigerant during the period from immediately before the beginning of ejection of the refrigerant to completion of the ejection and, then, release the vent orifice to allow the refrigerant to be gasified after completion of the ejection or a porous element enshrouding the container loaded into the cooling compartment and adapted to absorb the refrigerant from the cylinder in liquid form and, then, allow the refrigerant to be gasified around the article to be chilled.

10 Claims, 30 Drawing Sheets

PORTABLE CHILLER

This application is a continuation of application Ser. No. 705,672 filed May 24, 1991, now abandoned.

BACKGROUND OF THE INVENTION

1. Field of the Invention

The present invention relates to a portable chiller for a liquid pharmaceutical preparation, cosmetic preparation, beverage or the like which is available in a comparatively small container.

2. Brief Description of the Prior Art

Portable chillers of this type are disclosed in Japanese Kokai Tokkyo Koho No. 51-85546 and Japanese Kokai Jituyo Shinan Koho No. 60-125479, among others.

These known chillers generally comprise a housing for accommodating an article to be chilled, a cylinder filled with a compressed liquid refrigerant, a nozzle communicable with said housing and cylinder and adapted to deliver said compressed liquid refrigerant into said housing and a valve operable to open and close said nozzle.

The working principle of these prior art chillers is that as an article to be chilled, which may for example be a handkerchief, a bottled drug or a canned beverage, is accommodated in the housing and the valve is opened, the compressed liquid refrigerant is ejected from the nozzle of the cylinder into the housing to chill the article by the heat of vaporization.

In these prior art chillers wherein the article is directly exposed to the gasified refrigerant, the consumption of the refrigerant is high and the cylinder must be changed with high frequency. This is not only troublesome but also uneconomical. These problems could be solved by increasing the capacity of the refrigerant cylinder but this practice would increase the whole bulk of the chiller to cause inconveniences in carrying.

Moreover, since the refrigerant impinges only on a limited surface, i.e. on the surface of the article that faces the nozzle, the cooling efficiency is inevitably low. This, in turn, means an increased consumption of the refrigerant to achieve the required chilling effect, amplifying the above-mentioned problems.

SUMMARY OF THE INVENTION

The present invention has been developed to overcome the above-mentioned disadvantages of the prior art chillers and has as its object to provide a portable chiller with remarkably increased chilling efficiency.

Another object of the invention is to provide a portable chiller which consumes a drastically reduced quantity of the refrigerant and, hence, does not require frequent change of the cylinder, thus being convenient and economical.

It is a further object of the invention to provide a portable chiller which, as a whole, can be small in size and easy to carry about.

The above and further objects, features and advantages of the invention will more fully appear from the following description with reference to the accompanying drawings. It is to be expressly understood, however, that the drawings are for purpose of illustration only and are not intended as a definition of the limits of the invention.

BRIEF DESCRIPTION OF THE DRAWINGS

FIG. 1 is a partially exploded overall perspective view of the portable chiller;

FIG. 2 is an overall perspective view of the same chiller;

FIG. 3 is a sectional view taken along the line III—III of FIG. 1;

FIG. 4 is a sectional view taken along the line IV—IV of FIG. 1; and

FIGS. 5 through 7 are sectional views each showing the operation of the chiller.

FIG. 8 is a perspective view, with the case cover open;

FIG. 9 is a plan view in partial section;

FIG. 10 is a sectional view taken along the line X—X of FIG. 9, with the cover closed;

FIG. 11 is a right side elevation view, with the cover closed;

FIG. 12 is a front view of the same; and

FIG. 14 is a perspective view;

FIG. 15 is a transverse section view;

FIG. 16 is a sectional view taken along the line XVI—XVI of FIG. 15;

FIG. 17 is a right side elevation view; and

FIG. 18 is a front view.

FIG. 19 is a perspective view;

FIG. 20 is a transverse section view;

FIG. 21 is a sectional view taken along the line XX—XX of FIG. 20;

FIG. 22 is a right side elevation view; and

FIG. 23 is a front view.

FIG. 24 is an overall perspective view and

FIG. 25 is a partial perspective view.

FIG. 27 is a front view;

DETAILED DESCRIPTION OF THE PREFERRED EMBODIMENTS

The present invention is now described in detail with reference to the accompanying drawings, taking a small-sized eyedrop container-dispenser as an example of the article to be chilled.

Figure 26:
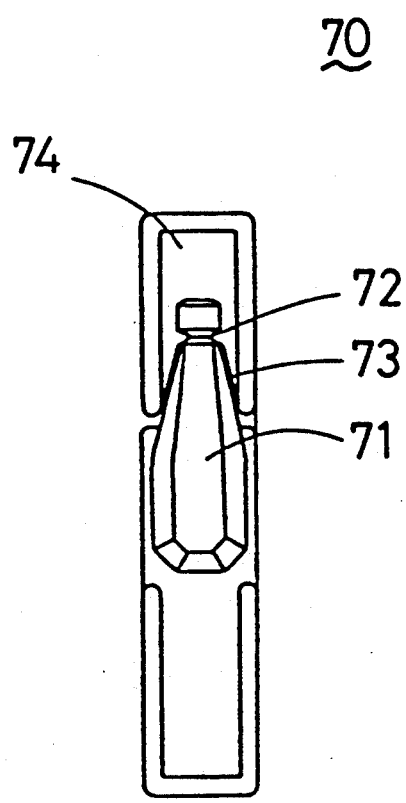
FIG. 26 is a front view showing an eyedrop container-dispenser as an example of the article to be chilled, which is used in the description of the first through sixth embodiments.

First, this eyedrop container 70, which will be referred to in the following detailed description of the preferred embodiments, is described in some detail. As illustrated in FIG. 26, this eyedrop container-dispenser 70 comprises a container 71 which is a rectangular plastic strip locally bulged out to form a housing in which an ophthalmic solution in a quantity equivalent to a single instillation dose is hermetically contained. On either side of the housing 71 and colose to its neck portion 72 is an incision 73 so that in using the eyedrop a tear-off portion 74 is held and torn off along said incision 73 to expose the neck 72. Then, the housing 71 is pressed with fingers to drip the ophthalmic solution from the neck 72. After installation, the whole container is discarded.

EXAMPLE 1

Figure 1:
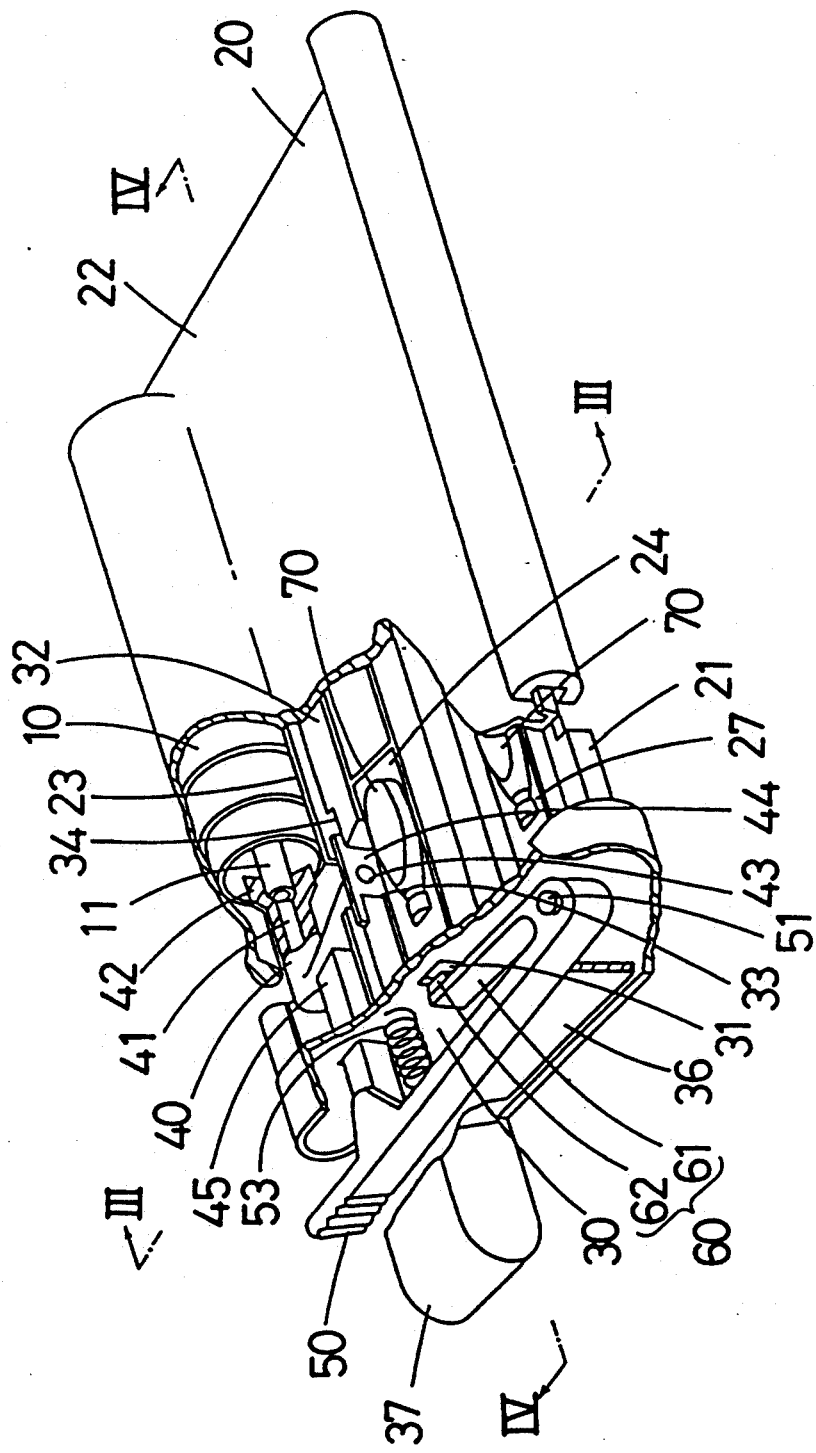
FIGS. 1 through 7 show a portable chiller as a first embodiment of the invention; wherein—
Figure 2:
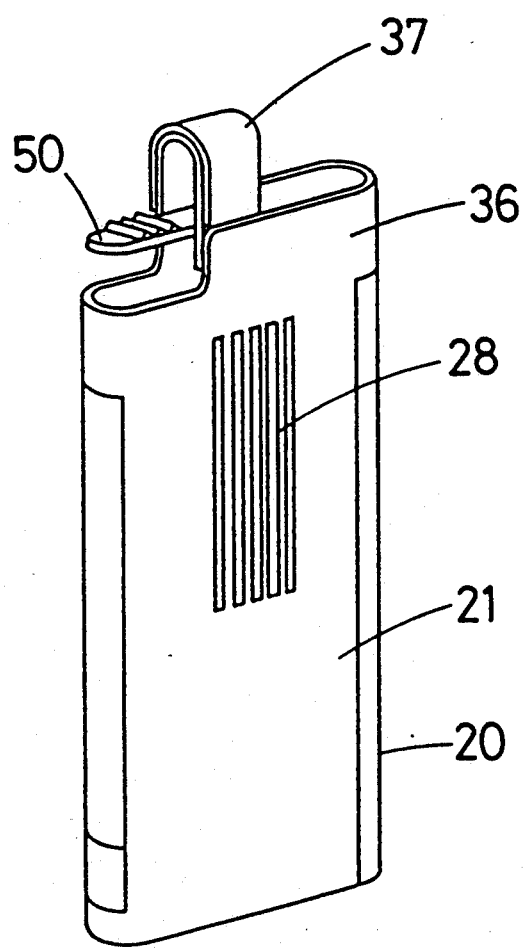
Figure 3:
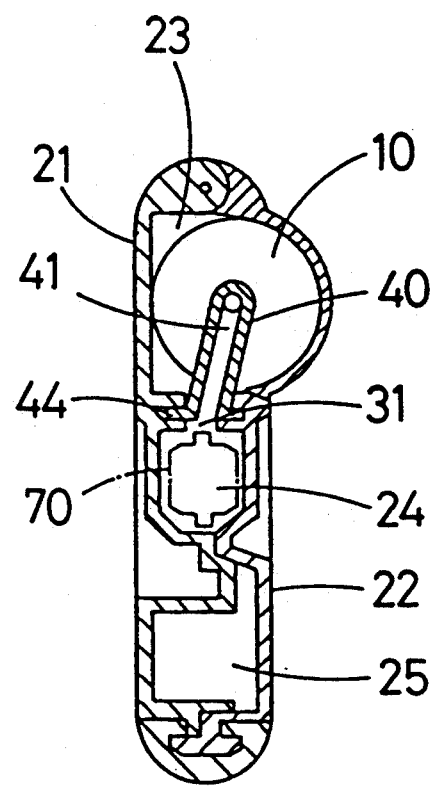
Figure 4:
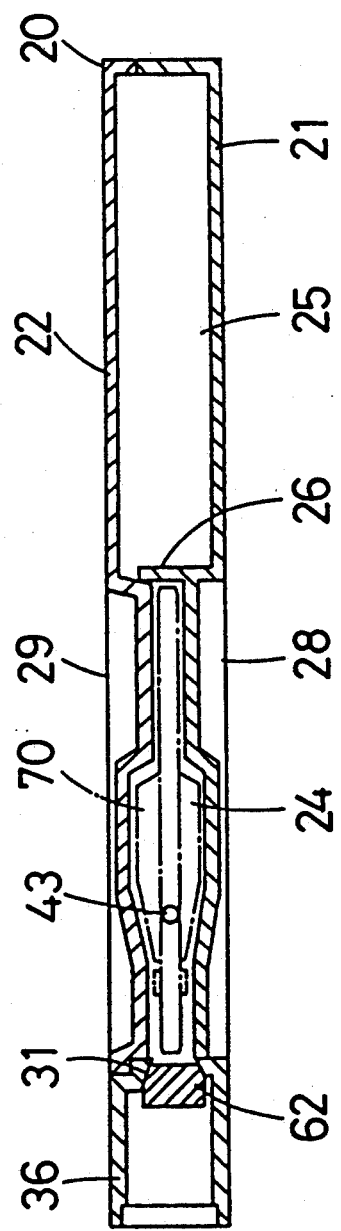
Figure 5:
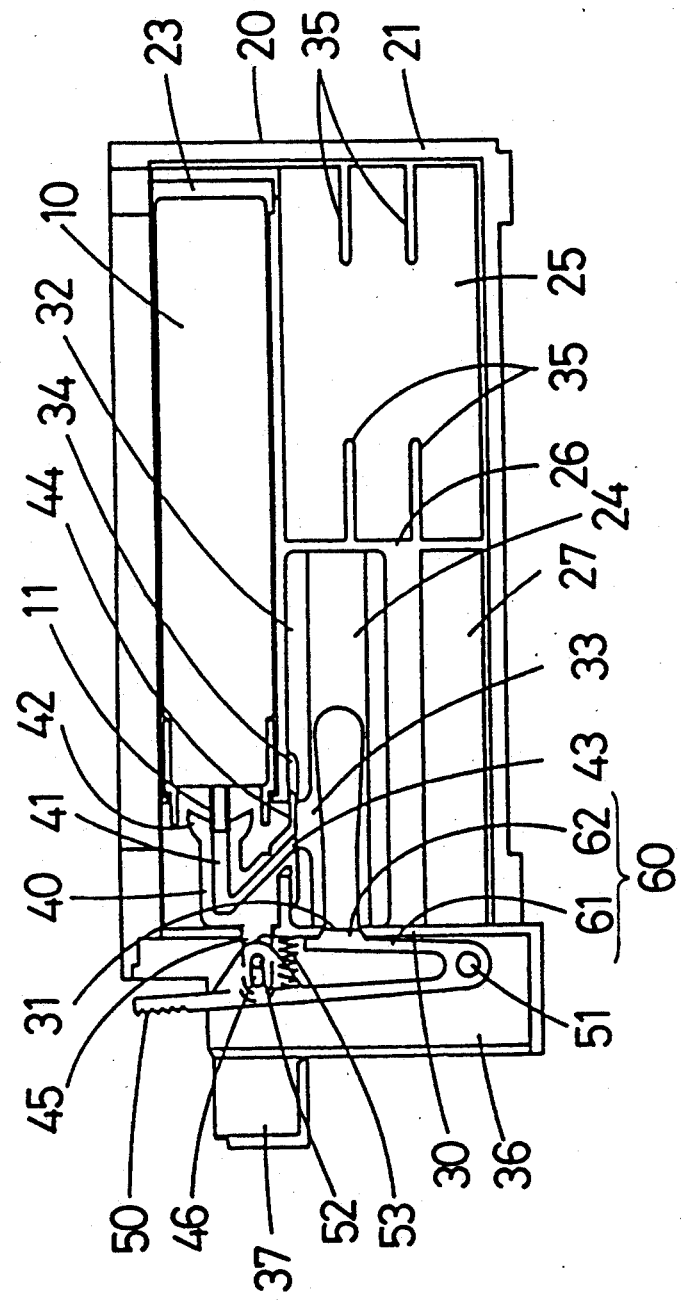
Figure 6:
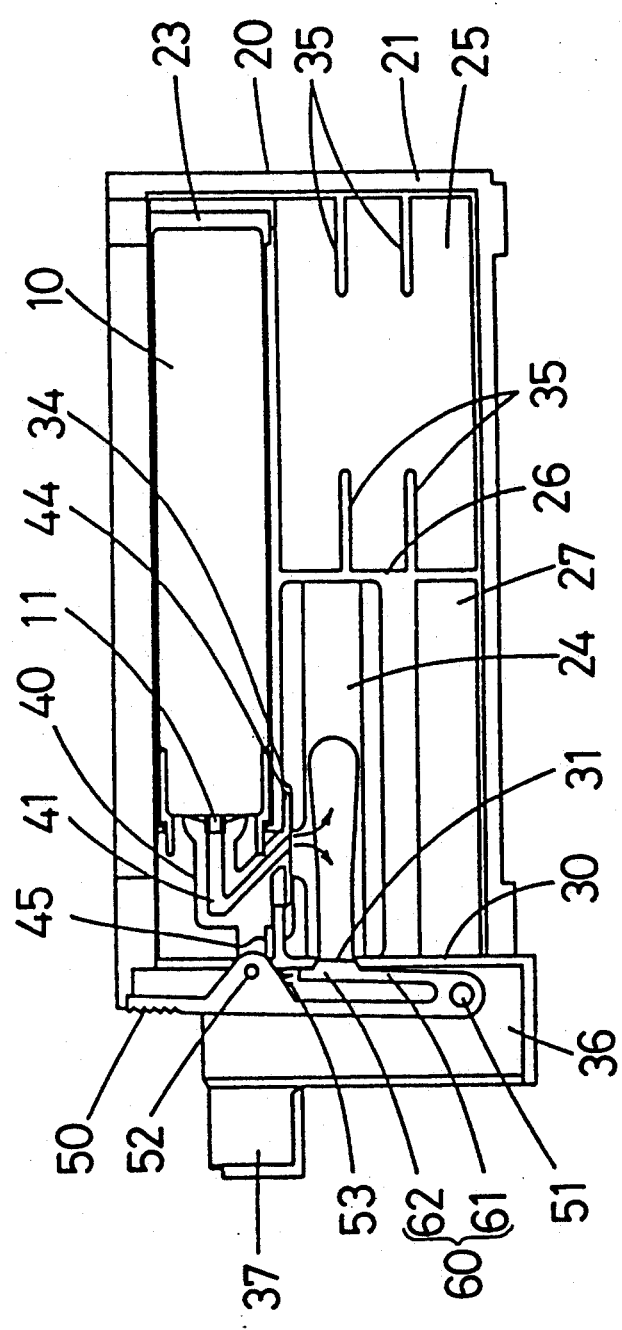
Figure 7:
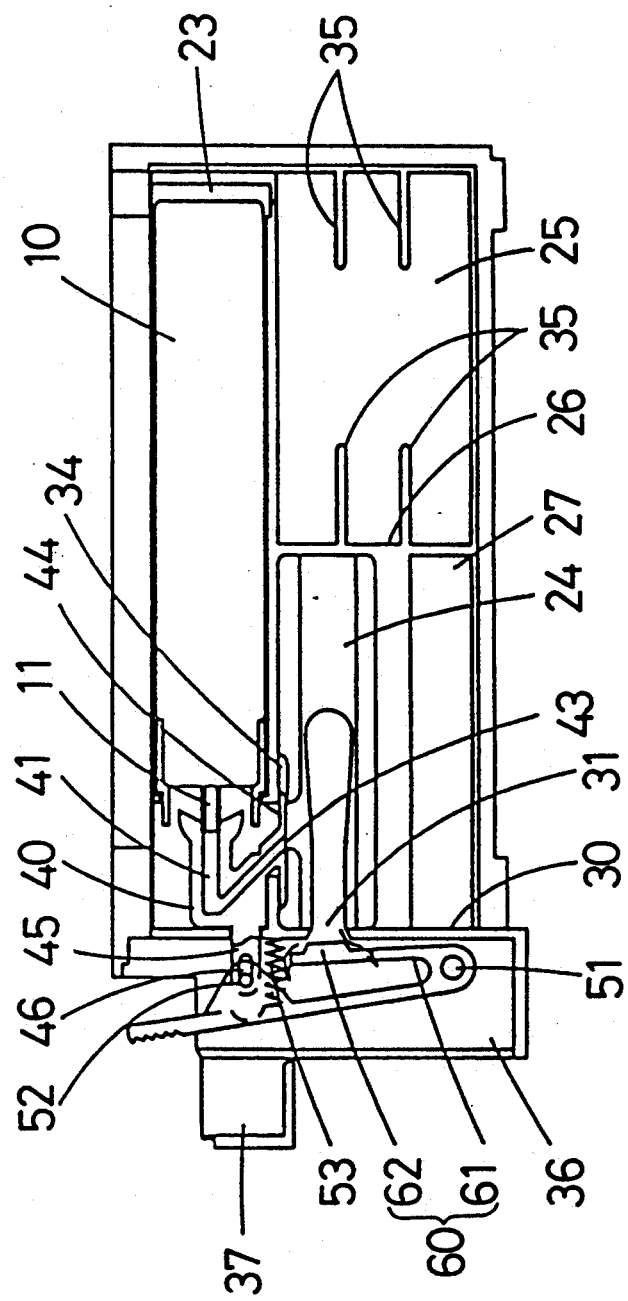

The first embodiment of the present invention is illustrated in FIGS. 1 through 7. FIG. 1 is a partially exploded overall perspective view; FIG. 2 is an overall perspective view; FIG. 3 is a sectional view along the line III—III of FIG. 1; FIG. 4 is a sectional view along the line IV—IV of FIG. 1; and FIGS. 5 through 7 are sectional views showing the action of the embodiment.

This portable chiller generally comprises a refrigerant cylinder 10 and a chiller case 20.

The cylinder 10 contains a refrigerant which has been compressed into a liquid. The refrigerant may be any of nontoxic substances commonly employed for this kind of refrigeration, such as a fluorocarbon (Freon ®, dupont), carbon dioxide, methyl chloride, butane and so on. To the forward end of this cylinder 10 is affixed a nozzle 11 in such a manner that as the nozzle 11 is forced into the cylinder 10, said refrigerant within the cylinder 10 is ejected via the nozzle 11.

The chiller case 20 may be made of synthetic resin or metal, e.g. aluminum, and comprises a case body 21 and a cover 22.

The case body 21 is formed, along one side thereof, with a cylinder compartment 23 for accepting the cylinder 10 and, alongside this cylinder compartment 23, a cooling compartment 24 and a compartment 25 for housing an article to be chilled are disposed in juxtaposition through a partitioning wall 26. In addition, a compartment 27 for housing additional articles to be chilled are further disposed on the opposite side of the cooling compartment 24 with respect to the cylinder compartment 23. Moreover, the back of this case body 21 is provided with a plurality of ribs 28 for insuring a cooling effect in the position corresponding to the cooling compartment 24.

The aforesaid cover 22 releasably closes said cylinder compartment 23, cooling compartment 24 and compartments 25, 27 for housing articles to be chilled. This cover 22 is swingably supported by a hinge (not shown) about an edge of the case body 21 which is closer to the cylinder compartment 23 and can be set in position on the case body 21 with an appropriate engaging means (not shown) disposed at its free end. Moreover, the part of said cover 22 which corresponds to said cooling compartment 24 is configurated to be generally complementary with the top configuration of the eyedrop container 70 (the article to be chilled) so that, upon closing the cover 22, the cooling compartment 24 is shut off as shown in FIGS. 3 and 4. The said part corresponding to the cooling compartment 24 is also externally provided with a plurality of ribs 29 for insuring a cooling effect just as in the case of the ribs located on the case body 21.

The cooling compartment 24 is adapted to chill the eyedrop container 70 (the article to be chilled loaded therein) and, as illustrated in FIGS. 3 and 4, this internal wall surface is configured to be generally complementary with the exterior contour of the eyedrop container 70. While this cooling compartment 24 is secluded hermetically as said cover 22 is set in position as mentioned above, it is so arranged that a clearance is formed between the internal wall surface (the inner surface of the cover 22 and the side and bottom surfaces of the cooling compartment 24) and the eyedrop container 70 on closing so that the refrigerant may circulate around the eyedrop container 70. Furthermore, a vent orifice 31 is formed in the wall of this cooling compartment 24 which lies opposite to said partitioning wall 26 (i.e. the side wall 30 of case body 21). This vent orifice 31 has an inner peripheral surface tapered toward the cooling compartment 24 so that it is smaller in sectional area on the side of the cooling compartment 24. Moreover, a refrigerant inlet 33 is formed in a side wall 32 of this cooling compartment 24 which is closer to the cylinder compartment 23. This refrigerant inlet 33 is an opening elongated in the longitudinal direction of the cooling compartment 24 and is flared toward the cooling compartment 24. In addition, a recess 34 is formed in the wall around the open end of said refrigerant inlet 33 which is farther from the cooling compartment 24.

The compartments 25, 27 are adapted to accommodate a plurality of spare (four in the illustrated embodiment) eyedrop containers 70. Provided in the compartment 25 are two pairs of juxtaposed projections 35 which are adapted to retain the eyedrop container 70 in position. It should be understood that these compartments 25, 27 for housing articles to be chilled need not necessarily be formed integrally with the case body 21 as in this embodiment but it may be so arranged, for instance, that a magazine carrying a plurality of eyedrop containers is loaded into the case body 21.

The chiller case 20 has an adapter 40 and a lever 50, which constitute a refrigerant ejection means.

The adapter 40 is disposed slidable in the axial direction of the cylinder 10 in the depth of the cylinder compartment 23. This adapter 40 is designed to introduce the refrigerant from a nozzle 11 of the cylinder 10 in the cylinder compartment 23 into said cooling compartment 24 and has a refrigerant passageway 41 extending therethrough. The adapter 40 is configured generally in the shape of the letter L, with one end thereof forming a nozzle socket 42 enlargeable with the tip of said nozzle 11 of cylinder 10, while the other end forming a refrigerant ejector 43 adjoining to said cooling compartment 24. This refrigerant ejector 43 has a rectangular collar 44 around it and this collar 44 is slidably fitted into said recess 34 to obstruct said refrigerant inlet 33 so that the refrigerant will not leak from the cooling compartment 24 into the cylinder compartment 23. Extending from the bend of this adapter 40 through a side wall 30 of the case body 21 is a connecting rod 45 for connection to said lever 50.

The lever 50 functions to actuate ejection of the refrigerant from the cylinder 10 accommodated in the cylinder compartment 23. This lever 50 is disposed inside of a cover 36 formed integrally with the case body 21 via said side wall 30 and its base end portion is pivotally attached to a pin 51 projection from the internal wall of the cover 36 in parallel with said side wall 30. On the other hand, the forward end portion of said lever 50 is connected to said connecting rod 45. This connection to the connecting rod 45 is effected, as shown in FIG. 5, by fitting a connecting pin 52 disposed on the underside of the forward end portion of the lever 50 loosely into an axially elongated slot 46 (FIG. 5) of the connected rod 45 in such a manner that the connecting rod 45 is displaced toward the cylinder 10 only after the lever 50 is depressed by the distance equal to the length of the elongated slot 46. Connected to an intermediate position of this lever 50 is one end of a coil spring 53, the other end of which is secured to the side wall 30, whereby the lever 50 is normally preenergized away from the side wall 30. Moreover, the forward end of the lever 50 is protected by a snap-up protective cap 37.

Disposed within said cover 36 is a vent closure member 60 constituting a refrigerant gasification control means. This vent closue member 60 keeps closing the vent orifice 31 of said cooling compartment 24 during the period from immediately before the beginning of ejection of the refrigerant by the refrigerant ejection means to completion of the refrigerant ejection to thereby withhold gasification of the refrigerant for a while and, then, open the vent orifice 31 to allow gasification of the refrigerant. This vent closure member 60 comprises an arm 61 formed integrally with the base of said lever 50 and a sealing plug 62 disposed at the end of the arm 61. The arm 61 is made of an elastic material and is, therefore, flexible. The sealing plug 62 is either integral with the arm 61 or a discrete unit secured rigidly to the end of the arm 61. When it is a discrete unit secured to the arm 61, the plug 62 can conveniently be made of a resilient material, such as rubber, which is excellent in sealing effect. This sealing plug 62 is configured to be complementary with the vent orifice 31 having an internally tapered surface so that it may positively plug off the vent orifice 31. This vent closure means 60 is normally in a position leaving the vent orifice 31 open but as said lever 50 is depressed, the means 60 is pivotally displaced toward the vent orifice 31 to close the vent orifice 31 with its sealing plug 62.

The method for use of the above-described portable chiller is now described with reference to FIGS. 5 through 7. In these views, the eyedrop container 70 is not shown.

First, the cover 22 of the chiller case 20 is opened and the cylinder compartment 23 is loaded with the cylinder 10. In this procedure, the nozzle 11 of the cylinder 10 is fitted into the nozzle socket 42 of the adapter 40.

Then, one of the eyedrop containers 70 is taken out from the compartment 25 or 27 and set it in position within the cooling compartment 24.

After completion of this loading with the eyedrop container 70, the cover 22 is replaced onto the case body 21, whereby the cooling compartment 24 is hermetically sealed off except at the vent orifice 31.

Then, the lever protective cap 37 is snapped up to expose the forward end of the lever 50. Then, as this forward end of the lever 50 is depressed against the biasing force of the coil spring 53, the arm 61 of the vent closure member 60 is pivotally displaced toward the side wall 30 of the case body 21 to ultimately bring the sealing plug 62 of the member 60 into the vent orifice 31 (FIG. 5). In this procedure, the connecting pin 52 of the lever 50 is shifted only within the elongated slot 46 of the connecting rod 45 so that the connecting rod 45 is not disturbed by the depression of the lever 50. In other words, ejection of the refrigerant does not begin as yet.

As the lever 50 is further depressed from the above position, the arm 61 of the vent closure member 60 is flexed and the connecting rod 45 is pressed by the connecting pin 52 of the lever 50 at its elongated slot 46 and displaced toward the cylinder 10, whereupon the adapter 40 also slides toward the cylinder 10. As the adapter 40 slides toward the cylinder 10 in this manner, the nozzle 11 is pressed into the cylinder 10 and, as a consequence, the refrigerant in the cylinder 10 is ejected through the refrigerant passageway 41 within the adapter 40 into the cooling compartment 24 (as indicated by the arrowmarks in FIG. 6). As the refrigerant is ejected into the cooling compartment 24 closed hermetically in the described manner, a high pressure is established in the cooling compartment 24 and the compartment 24 is impregnated with the liquid refrigerant not yet gasified despite ejection.

Thus, in the cooling compartment 24, the eyedrop container 70 is immersed in the liquid refrigerant.

As the cooling compartment 24 becomes full of the refrigerant and attains a high internal pressure, the ejection of the refrigerant from the cylinder 10 is automatically stopped by the very high pressure.

As the ejection stops, the lever 50 is released, whereupon the recovery force of the arm 61 and coil spring 53 causes the lever 50 to return to its ininital position. As a consequence, the adapter 40 also returns to its original position and the sealing plug 62 is released from the vent orifice 31 of the cooling compartment 24. Since the hermetic seal of the cooling compartment 24 is thus broken, the liquid refrigerant in high-pressure condition in the cooling compartment 24 is instantly gasified as it deprives the eyedrop container 70 of heat and the resultant refrigerant gas is vented from the chiller case 20 through the vent orifice 31 (as indicated by the arrowmark in FIG. 7). In this manner, the eyedrop container 70 as a whole is instantly chilled.

After waiting till the time when the chilling of the eyedrop container 70 is completed, the cover 22 is opened and the chilled container 70 is taken out from the cooling compartment 24 for installation.

While, in the above embodiment, the refrigerant ejection means (adapter 40 and lever 50) and the refrigerant gasification control means (vent closure member 60) are operatively associated, the invention may be embodied in such otherwise fitted into the vent orifice of the cooling compartment and after completion of the refrigerant ejection it is removed manually or otherwise.

EXAMPLE 2

Figure 8:
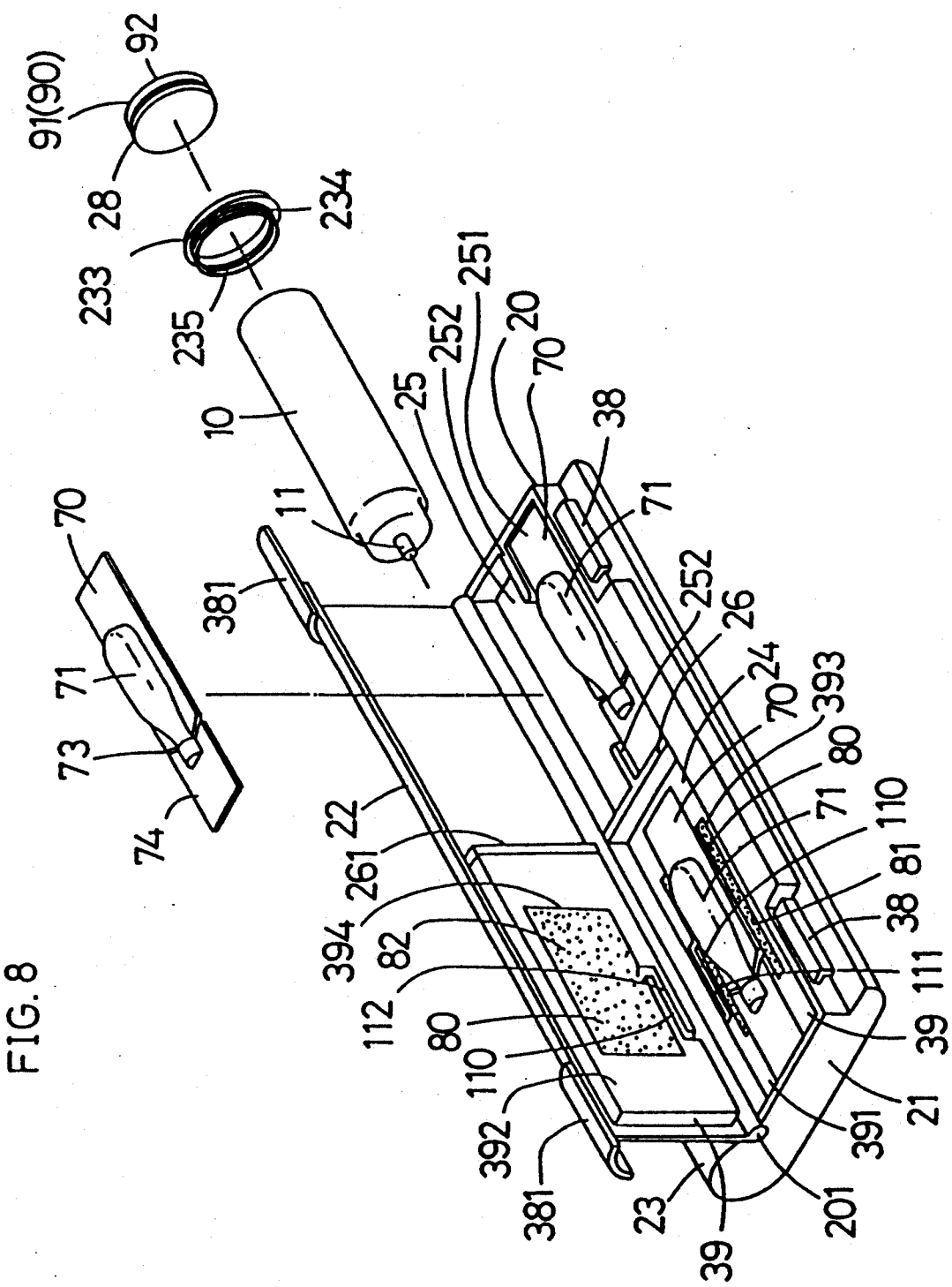
FIGS. 8 through 12 show a portable chiller as a second embodiment of the invention; wherein—
Figure 9:
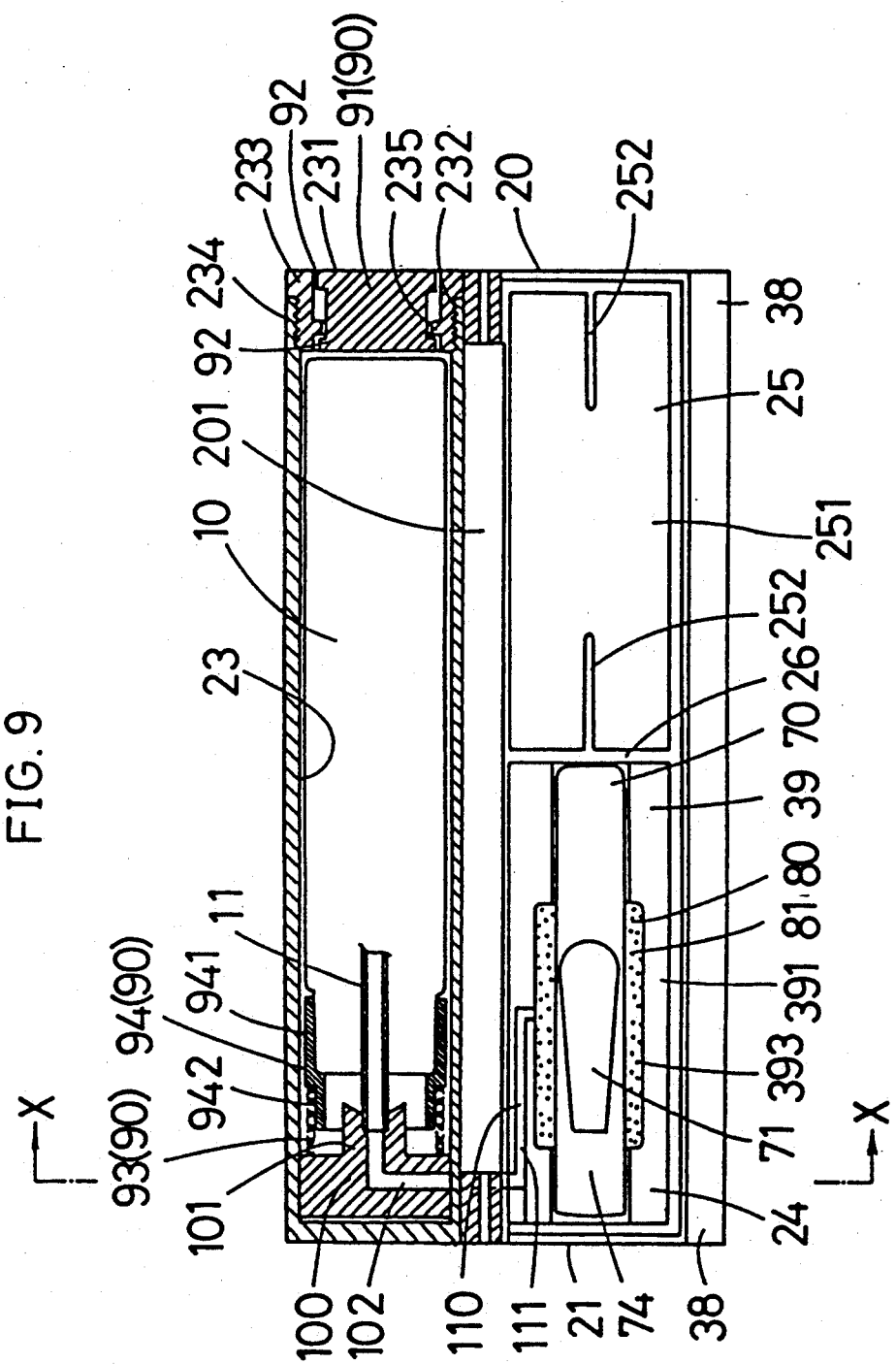
Figure 10:
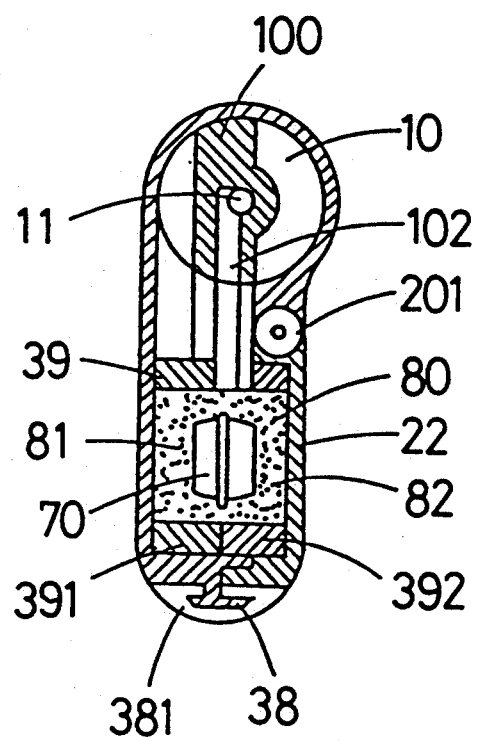
Figure 11:
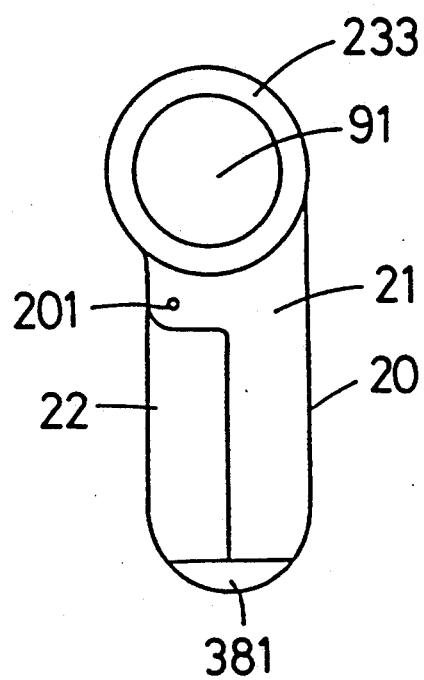
Figure 12:
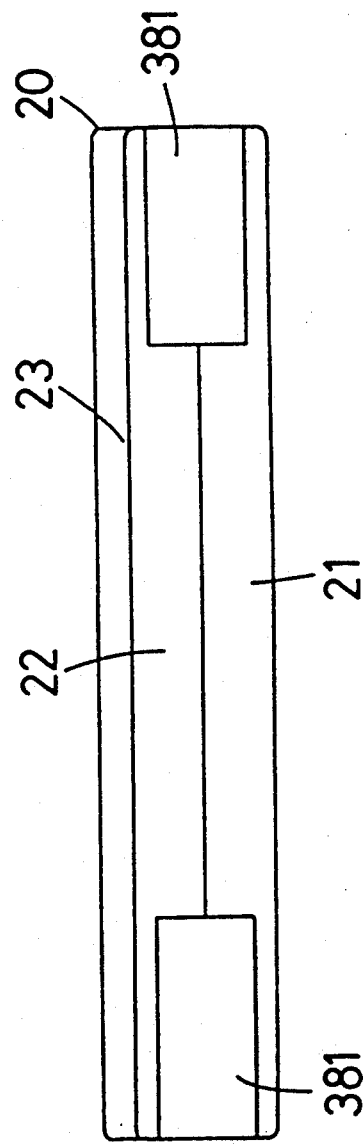

FIGS. 8 through 12 show another embodiment. FIG. 8 is a perspective view of the same with the case cover opened; FIG. 9 is a plan view in partial section; FIG. 10 is a sectional view taken along the line X—X of FIG. 9, with the cover closed; FIG. 11 is a right side elevation view, with the cover closed; and FIG. 12 is a front view of the same.

In the following description, the like parts are indicated by the like numerals used for the preceding embodiment.

This portable chiller generally comprises a cylinder 10, a chiller case 20 and a porous element 80.

The construction of the cylinder 10 is similar to that of the first embodiment and, therefore, not described.

The chiller case 20, which is also similar to that described for the first embodiment, is mede of synthetic resin or metal, such as aluminum, and consists of a case body 21 and a cover 22.

The case body 21 is formed, along its one side, with a cylinder compartment 23 for accepting said cylinder 10, and side-by-side with this cylinder compartment 23, a cooling compartment 24 and a compartment 25 for housing an article to be chilled are formed in juxtaposition as interrupted by a partitioning wall 26. This cylinder compartment 23 is provided with a refrigerant ejection means 90. The case body 21 is provided with a couple of cover stoppers 38, 38 toward both ends along the edge opposite to the edge along which said cylinder compartment 23 is disposed.

The cylinder compartment 23 is open for accepting the cylinder 10 at its end closer to the compartment 25 as indicated by 231. The internal peripheral surface of this cylinder loading port 231 is formed with a female thread 232 and this port 231 is opened and closed with a cap 233 which is engageable with this female thread 232. This cap 233 is in the form of a short cylinder with its peripheral surface having a male thread 234 adapted to mesh with said female thread 232 and its inner peripheral surface being formed with a circumferentially extending annular stopper projection 235.

Loosely fitted into this cap 233 is an ejection button 91 forming a part of said refrigerant ejection means 90 in such a manner that it can slide in the axial direction of the cap 233. This ejection button 91 is formed with stopper collars 92, 92 at both ends and as these stopper collars 92, 92 engage said stopper projection 235, this ejection button 91 is prevented from slipping out from the cap 233.

Securely installed in the depth of the cylinder compartment 23 is an adapter 100, while a coil spring 93 and a socket 94 each constituting a part of said refrigerant ejection means 90 are disposed slidably in the axial direction of this compartment 23.

The aforesaid adapter 100 functions to introduce the refrigerant from the nozzle 11 of the cylinder 10 set in the cylinder compartment 23 into said cooling compartment 24. This adapter 100 is formed, at its front side (the side facing the cylinder loading port 231), with a nozzle socket 101 for accepting the tip of the nozzle 11 of the cylinder 10 and internally with a refrigerant passageway 102 communicating with the nozzle socket 101 and cooling compartment 24.

The aforesaid coil spring 93 and socket 94 are adapted to constantly preenergize the cylinder 10 in the cylinder compartment 23 toward the ejection button 91 in the cylinder loading port 231. The coil spring 93 is biased between said adapter 100 and socket 94. The socket 94 consists of a large-diameter portion 941 bearing the forward end portion of the cylinder 10 and a smaller diameter portion 942 which is inserted into the coil spring 93.

The aforesaid cooling compartment 24 is a chamber in which a single eyedrop container 70 (the article to be chilled) is set in position and chilled and its length is approximately equal to that of the eyedrop container 70. Also disposed is a half member 391 constituting a holding frame 39 for retaining the eyedrop container 70 fixedly in position. This half member 391 is formed, on the top surface adjacent to said cylinder compartment 23, with a channel 111 constituting a part of a refrigerant line 110 communicating with the refrigerant passageway 102 of the adapter 100 in the cylinder compartment 23. Moreover, in an intermediate position of the half member 393, that is the position corresponding to the housing portion 71 of the eyedrop container 70, there is provided a porous element mount 393 and said channel 111 terminates in the center of this mount 393.

The aforesaid compartment 25 is designed to accommodate a plurality of spare eyedrop containers 70. In this embodiment, this compartment 25 is divided into two chambers, upper and lower, by a removable divider 251 so that a total of 4 containers 70, viz. 2 in the upper stage and 2 in the lower stage, can be accommodated. The divider 251 is formed with a pair of juxtaposed projections 252, 252 on each of its face and bottom sides, said each of projections extending from the center of the corresponding breadth of the divider, so that the eyedrop containers 70 accommodated on and under the divider 251 may be respectively held in position by said projections 252, 252.

The aforesaid cover 22 is intended to open and close the above-described cooling compartment 24 and compartment 25 for housing the article to be chilled. This cover 22 is pivotally connected to the case body 21 by a hinge 201 located between the cylinder compartment 23 and the cooling compartment 24 and compartment 25. Attached to both free ends of this cover 22 are locks 381, 381 which are adapted to engage the cover engaging members 38, 38 of case body 21 and slidable in the longitudinal direction of the cover 22 but inseparable from the cover 22. Furthermore, the inner side of this cover 22 is provided with a partitioning wall 261 in the position corresponding to the partitioning wall 26 between the cooling compartment 24 and compartment 25 of the case body 21 and a half member 392 constituting a part of said holding frame 39 in the position corresponding to the cooling compartment 24. Like the half member 391 on the case body 21 side, this half member 392 is formed with a channel 112 constituting the counterpart of said refrigerant line 110 on the side adjoining said hinge 201, that is to say the side facing the cooling compartment 24. Furthermore, a porous element mount 394 is disposed in an intermediate position of this half member 392, that is to say the position corresponding to the housing portion 71 of the eyedrop container 70 and said channel 112 terminates in the central part of this porous element mount 394.

The aforesaid porous element 80 serves to enclose the eyedrop container 70 set in the cooling compartment 24 of the chiller case 20 and absorbs the refrigerant ejected from the cylinder 10 in liquid form to assure a uniform gasification of the refrigerant around the eyedrop container 70. As examples of the material of such porous element 80 may be mentioned sponge, nonwoven fabric, paper, a synthetic rubber or urethane resin formed with a multiplicity of fine air cells. Among them, sponge is most advantageous in that it is not degraded at low temperature, this property being important because the temperature drops to near 0° C., is well penetrable by the refrigerant (liquid) and has a large air-entrapping capacity. The pores in this porous element 80 may be open at both ends or at one end only. Such porous element 80 is used as half members 81 and 82, one of which is attached to the porous element mount 393 of the case body 21 adjacent to its cooling compartment 24 and the other to the porous element mount 394 of the cover 22, with an adhesive or an adhesive tape.

The method for use of the portable chiller described above is explained below.

First, the cap 233 is disconnected from the cylinder loading port 231 of the case body 21 to open the cylinder loading port 231.

Then, the cylinder 10 containing the refrigerant is loaded, with its nozzle 11 forward, into the cylinder compartment 23 through said cylinder loading port 231 and the cap 233 is replaced by threading it onto the cylinder loading port 231. As the tip of the nozzle 11 of cylinder 10 is inserted into the nozzle socket 101 of the adapter 100, the tip of the cylinder 10 fits into the large-diameter portion 941 of the socket 94 and is subjected to the biasing force of the coil spring 93, whereupon the bottom surface of the cylinder 10 is pressed against the ejection button 91 within the cap 233 and the surface of the ejection button 91 becomes flush with the end face of the case body 21 and the surface of the cap 233.

Then, each of the locks 381, 381 of the case 20 is caused to slide outwardly to disengage the cover stoppers 38, 38 of the case body 21 and the cover 22 is opened.

Then, one eyedrop container 70 taken out from the compartment 25 is loaded into the cooling compartment 24 by setting it into the half members 391 of the holding frame 39.

After completion of this loading with the eyedrop container 70, the cover 22 is replaced into the closed position and the locks 381, 381 are slid in the reverse directions into engagement with the cover engaging members 38, 38 of the case body 21. By this procedure the eyedrop container 70 in the cooling compartment 24 is held in position by the holding frame 39 and the housing portion 71 of the container 70 as a whole is enshrouded by the porous element 80. As the half members 391, 392 of the holding frame 39 are thus mated, the channels 111, 112 formed on the top (opposed) surfaces of the respective half-members 391, 392 are lined up to form said refrigerant line 110.

Then, as the ejection button 91 is pressed against the biasing force of the coil spring 93, the nozzle 11 is subjected to a reaction from the nozzle socket 101 of the adapter 100 and pushed into the cylinder 10, whereby the refrigerant is ejected from the cylinder 10 through the nozzle 11, the refrigerant passageway 102 within the adapter 100 and the refrigerant line 110 within the holding frame 39 to the porous element 80 within the cooling compartment 24. The ejected refrigerant is not instantly gasified because of the presence of the porous element 80 but absorbed in the liquid state into the porous element 80. The refrigerant absorbed into the porous element 80 diffuses into the whole body of the element 80 under the influence of ejection pressure and capillary phenomen and deprives the porous element 80 and the air contained therein of heat. As a result, the whole porous element 80 is chilled and the housing portion 71 of the eyedrop container 70 which is enshrouded by the porous element 80 is also chilled from its entire surface.

After completion of the chilling, the locks 381, 381 of the chiller case 20 are disengaged, the cover 22 is opened, the chilled eyedrop container 70 is taken out, and the eyedrop is instilled.

EXAMPLE 3

Figure 13:
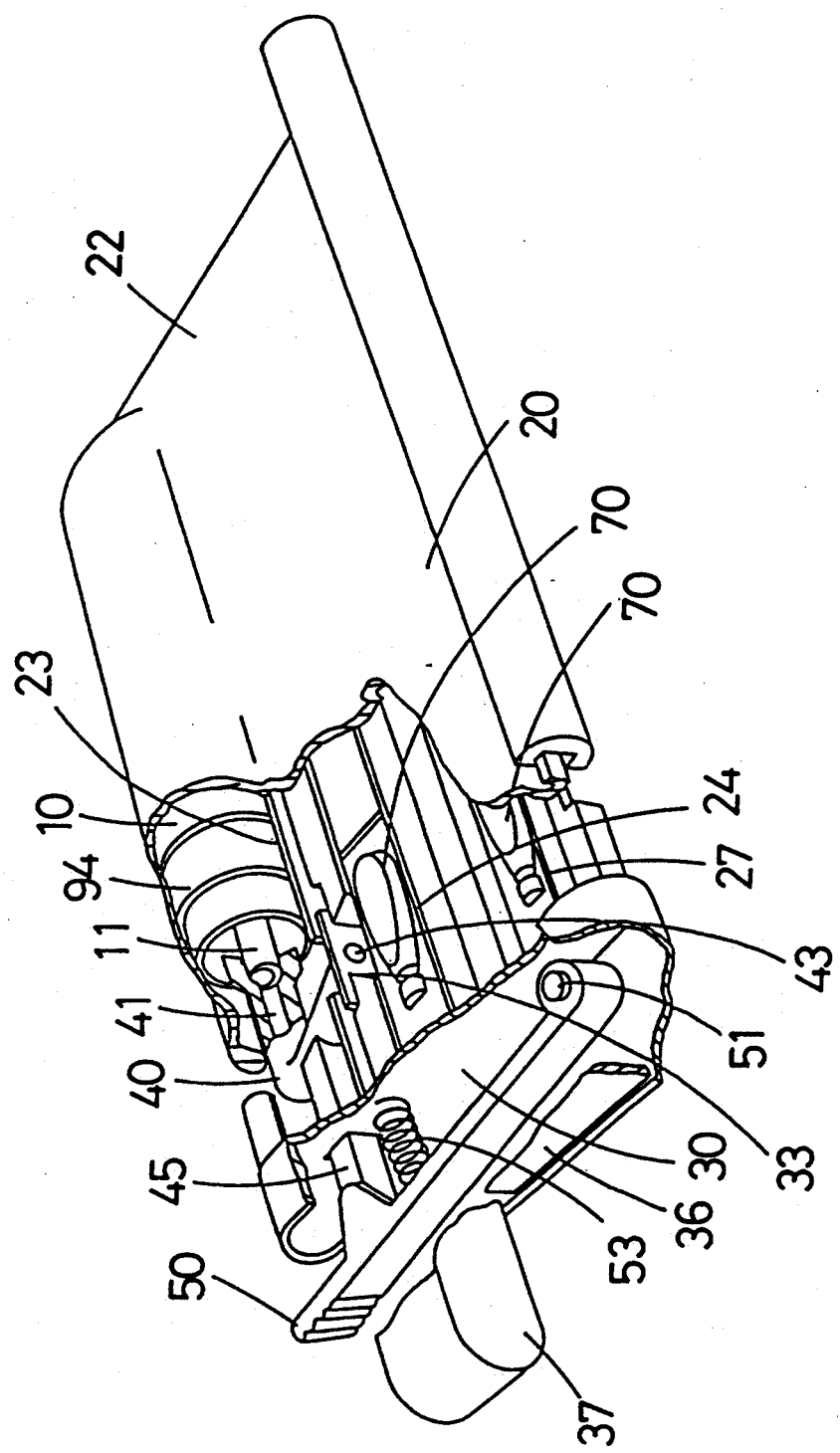
FIG. 13 is an overall perspective view in partial section showing a portable chiller as a third embodiment of the invention.

This third embodiment is illustrated in FIG. 13. It should be understood that the like parts are indicated by the like numerals used for the foregoing embodiments.

In this embodiment, the vent orifice 31 and the vent closure member 60 of the chiller case 20 are omitted and a porous element 80 is provided within a cooling compartment 24. The manner of use of this portable chiller is similar to that of the first embodiment. It should be understood that the elongated slot 46 of the connecting rod 45 is not essential and that the remainder of the construction is identical with that of the foregoing embodiment.

EXAMPLE 4

Figure 14:
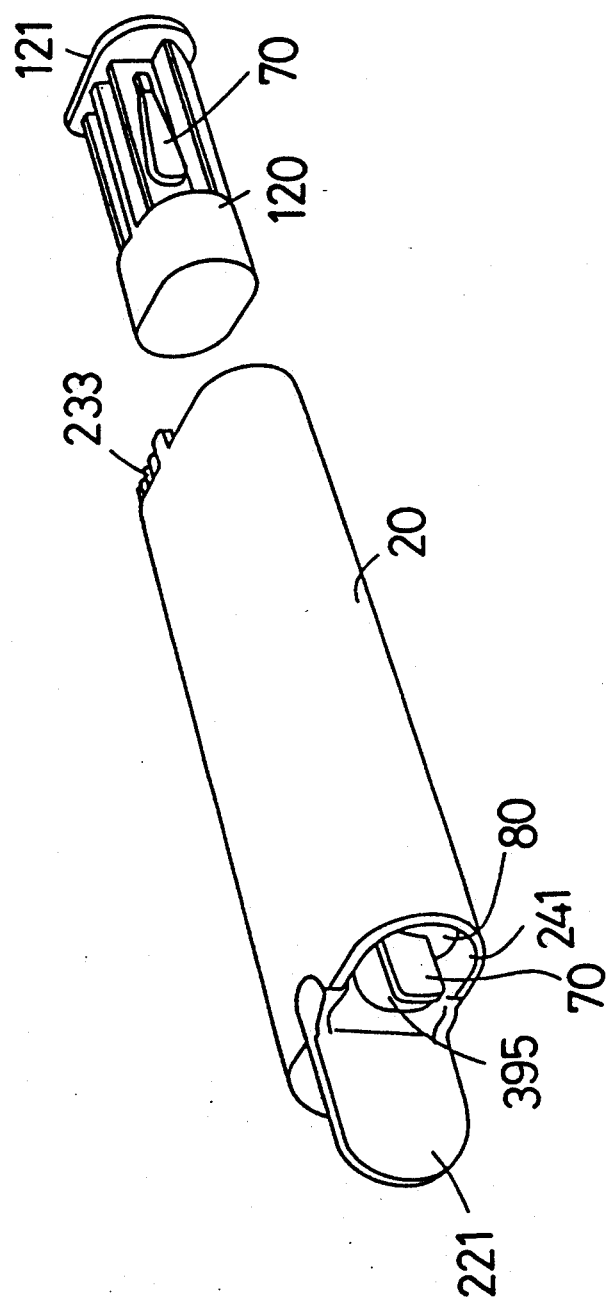
FIGS. 14 through 18 illustrate a portable chiller as a fourth embodiment of the invention; wherein—
Figure 15:
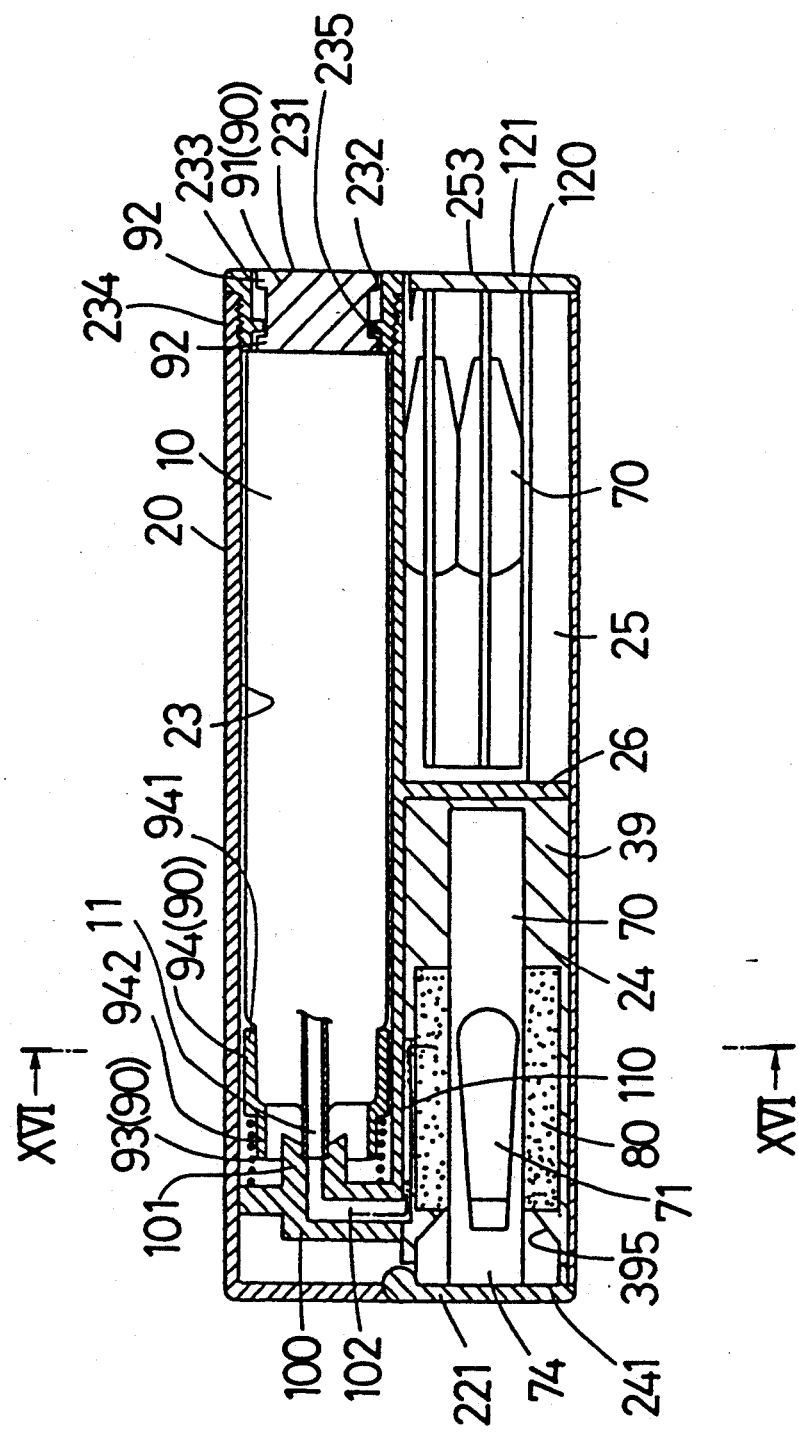
Figure 16:
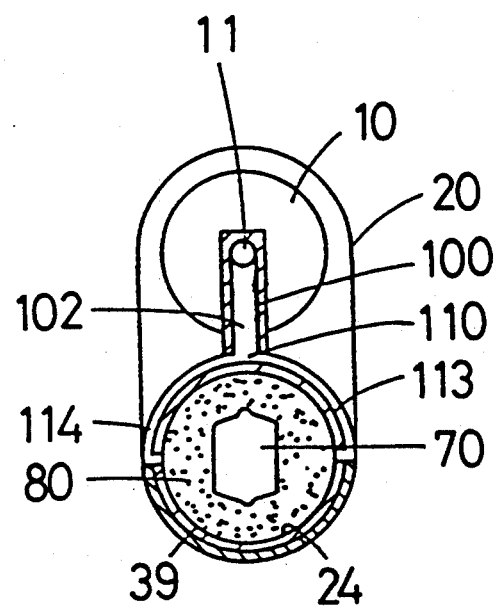
Figure 17:
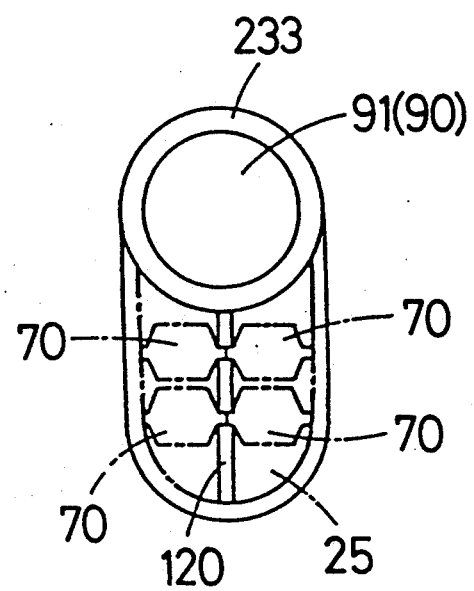
Figure 18:
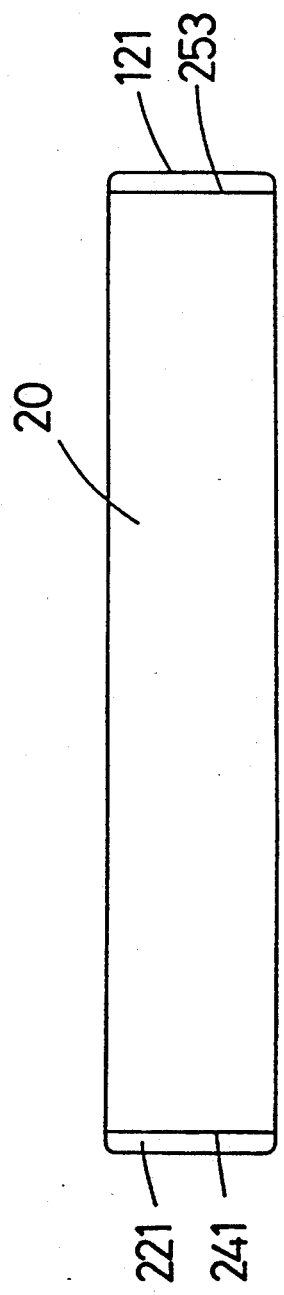

This embodiment is illustrated in FIGS. 14 through 18. FIG. 14 is a perspective view; FIG. 15 is a transverse section view; FIG. 16 is a sectional view taken along the line XVI—XVI of FIG. 15; FIG. 17 is a right side elevation view; and FIG. 18 is a front view. It should be understood that, in these views, the like parts are indicated by the like numerals used for the preceding embodiments.

In the following description, only the aspects that differentiate this embodiment from the foregoing embodiments are described.

In this embodiment, openings 241, 253 of the cooling compartment 24 and the compartment 25 for housing articles to be chilled are disposed at respective ends of the chiller case 20, and the opening 241 of the cooling compartment 24 is releasably closed with a cover 221.

The cooling compartment 24 is cylindrical and each of a holding frame 39 and a porous element 80 which are disposed therein is also a cylindrical member. The surface of the holding frame 39 which is facing said opening 241 is formed with a recess 395 so that the eyedrop container 70 may be easy to grip at its one end 74.

The refrigerant line 110 within the holding frame 39 is bifurcated to insure a more efficient absorption of the refrigerant into the porous element 80 and the terminals of these branch lines 113, 114 are disposed in the positions facing the housing portion 71 of the eyedrop container 70.

Installed in the compartment 25 for housing spare articles to be chilled is a magazine 120 and a plurality of eyedrop containers 70 are first set in this magazine 120 and loaded into the compartment 25. In the illustrated embodiment, four eyedrop containers 70 are accommodated in two rows and two stages. The bottom 121 of this magazine 120 doubles as a cover for opening and closing said opening 253.

To put this portable chiller to service, the cover 221 of the cooling compartment 24 is opened and an eyedrop container 70 is then inserted from its bottom end (the end opposite to the neck portion 72) into the cooling compartment 24 until a positive stop is felt. Then, the cover 221 is closed and the ejection button 91 is pressed to eject the refrigerant into the porous element 80.

The remainder of the construction is similar to that of the previous embodiments.

EXAMPLE 5

Figure 19:
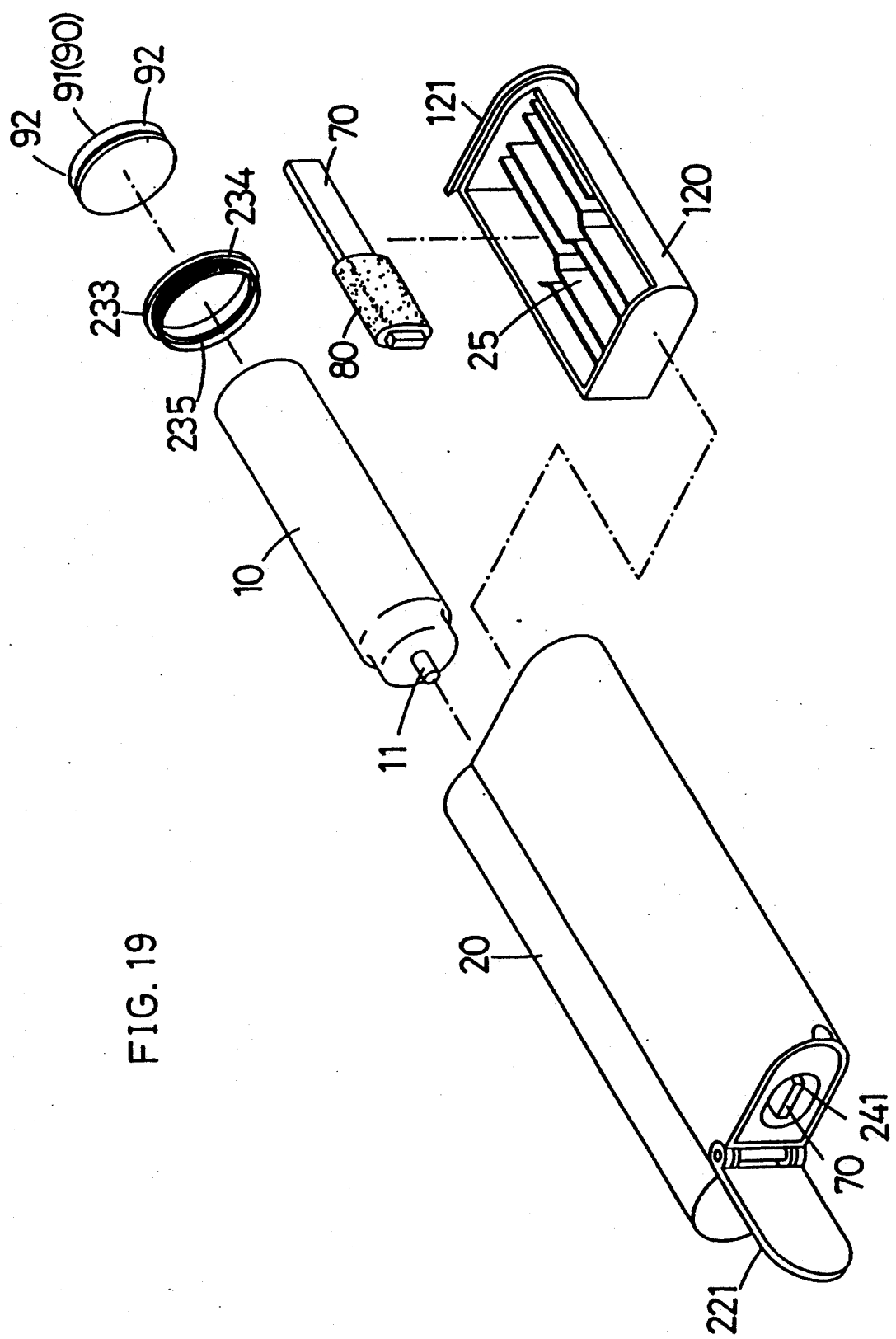
FIGS. 19 through 23 show a portable chiller as a fifth embodiment of the invention; wherein—
Figure 20:
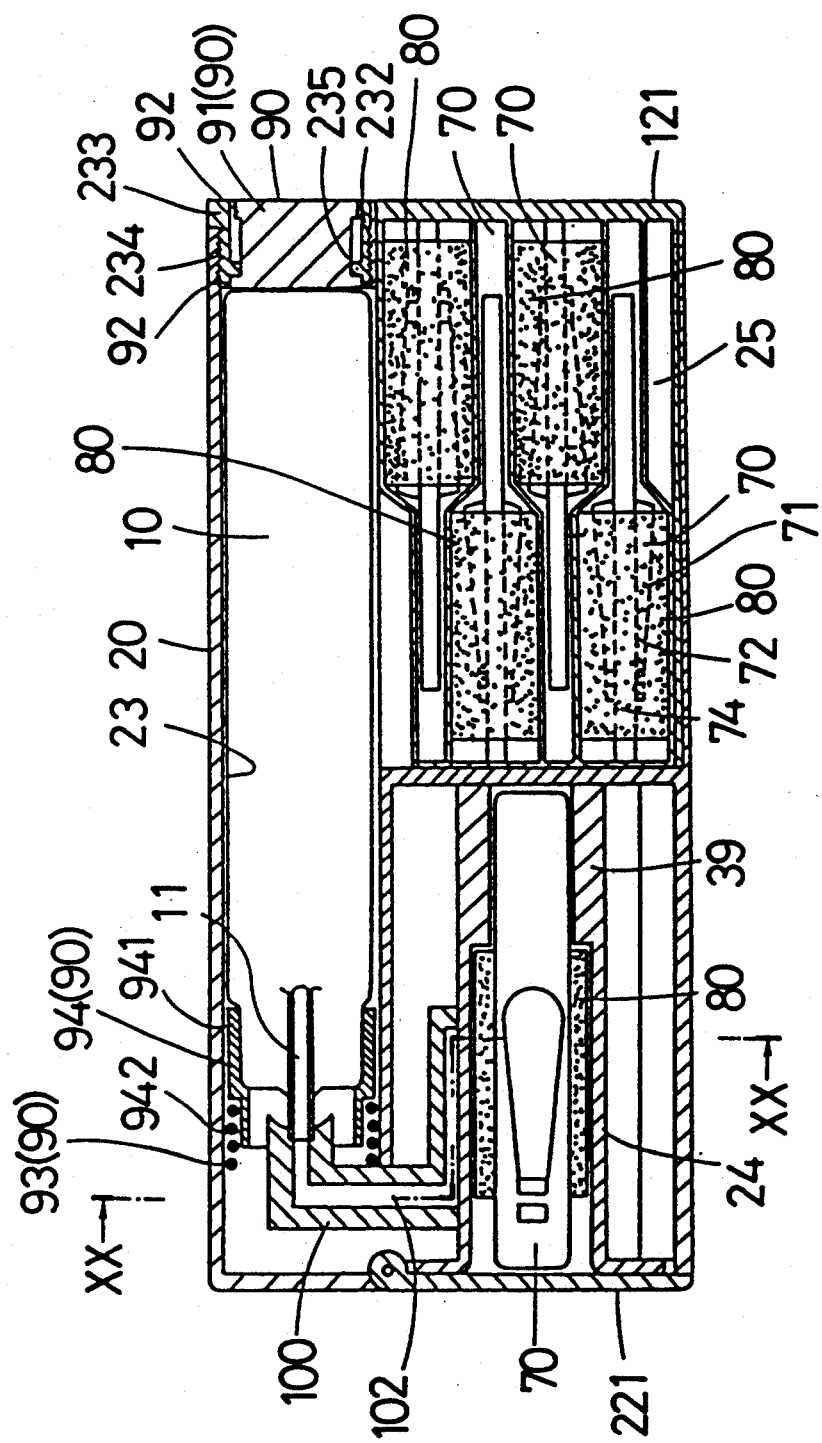
Figure 21:
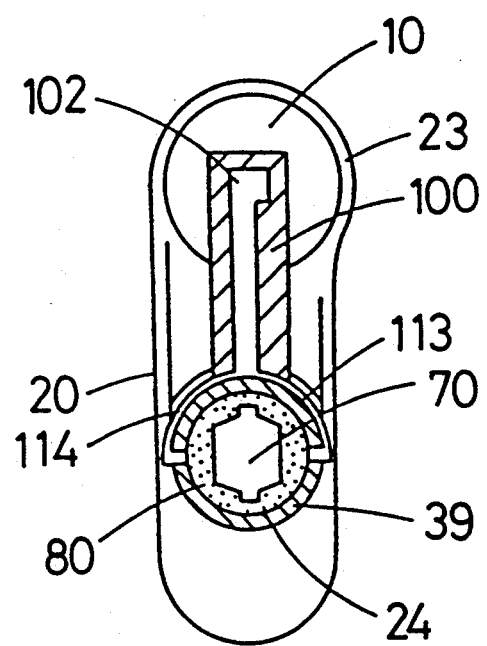
Figure 22:
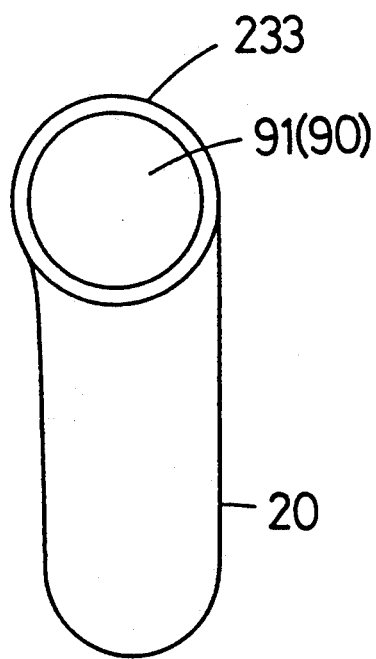
Figure 23:
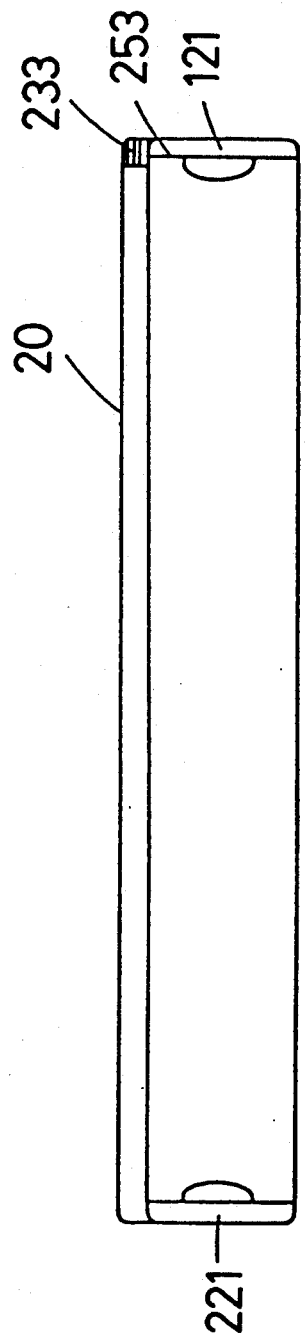

This fifth embodiment is illustrated in FIGS. 19 through 23. FIG. 19 is a perspective view; FIG. 20 is a transverse section view; FIG. 21 is a sectional view taken along the line XX—XX of FIG. 20; FIG. 22 is a right side elevation view; and FIG. 23 is a front view. It should be understood that the like parts are indicated by the like numerals used for the preceding embodiments.

Now, only the aspects that differentiates this embodiment from the preceding embodiment are described.

This embodiment is distinct in that the porous element 80 is not disposed in the cooling compartment 24. Thus, in this embodiment, the porous element 80 is formed as a cylinder which can be sleeved over the housing portion 71 of the eyedrop container 70 and has been previously fitted on each eyedrop container 70. After chilling, it is removed and discarded.

Since the porous element 80 is directly attached to the eyedrop container 70, the eyedrop container 70 carrying the porous element 80 is necessarily bulky but to compensate for this disadvantage, the magazine 120 loaded into the compartment 25 is divided ingeniously to permit efficient accommodation of eyedrop containers 70 and, hence, effective utilization of available space of the compartment 25.

The remainder of the construction of this portable chiller is similar to that of the foregoing embodiments.

EXAMPLE 6

Figure 24:
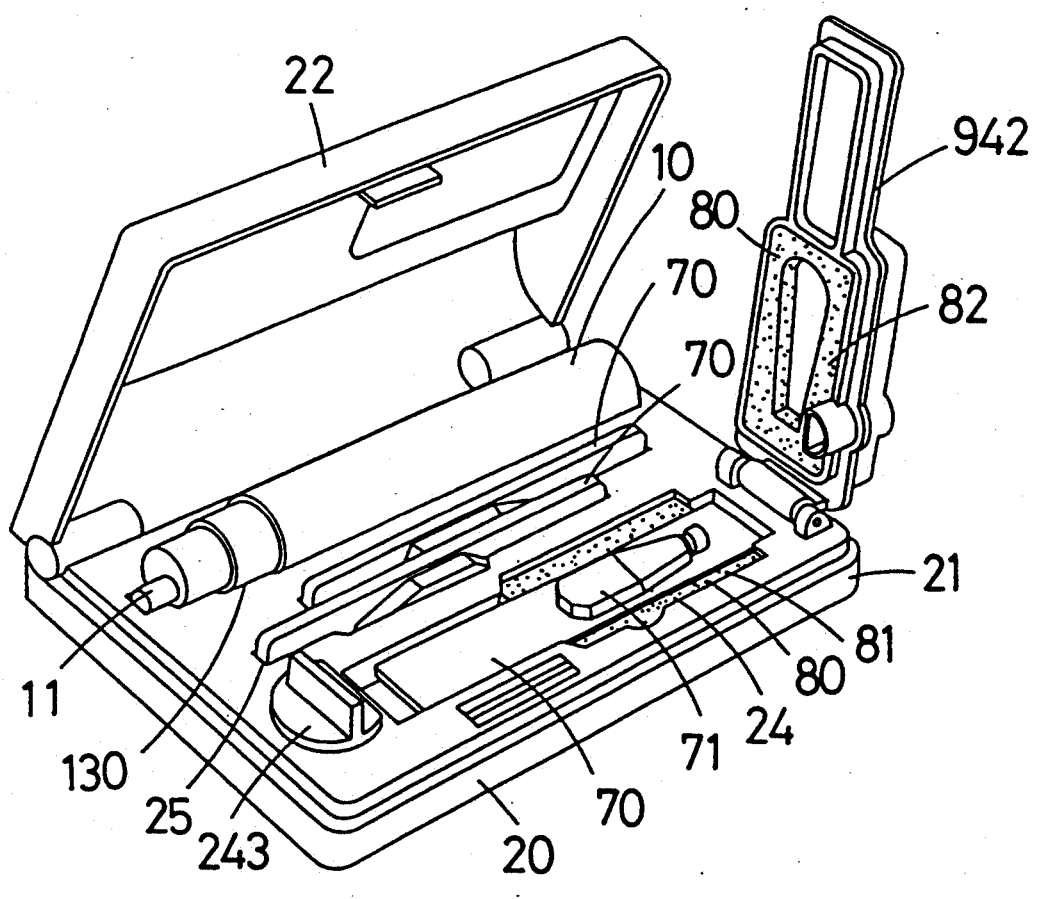
FIGS. 24 and 25 show a portable chiller as a sixth embodiment of the invention; wherein—
Figure 25:
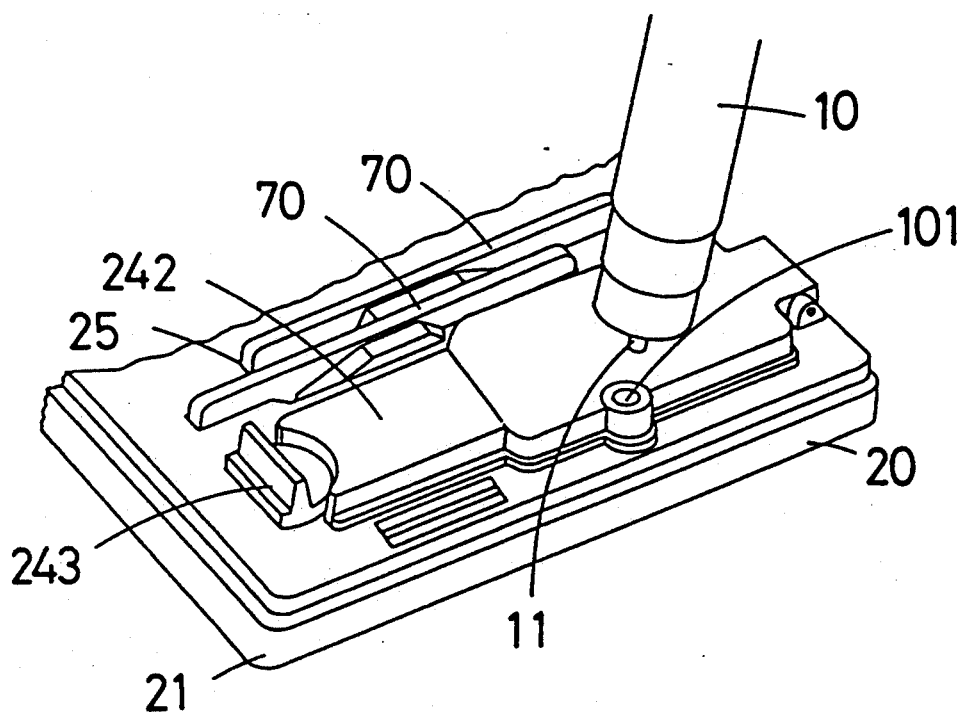

The sixth embodiment of the invention is illustrated in FIGS. 24 and 25. FIG. 24 is an over all perspective view and FIG. 25 is a partial perspective view. It should be understood that the like parts are indicated by the like numerals used for the preceding embodiments.

This embodiment is distinct in that the refrigerant is ejected from the cylinder 10 held in hand.

Thus, the chiller case 20 comprises a case body 21 and a cover 22 for opening and closing it, and a cylinder compartment 130, a compartment 25 for housing spare articles to be chilled, and a cooling compartment 24 are disposed in parallel on the top side of the case body 21. The cylinder compartment 130 and the compartment 25 for holding articles to be chilled are respectively formed as recesses complementary with the corresponding articles to be accommodated. The cooling compartment 24 is opened and closed with an inner cover 242 pivotally connected to the-top surface of the case body 21 and the cooling compartment 24 is completely sealed off as this inner cover 242 is closed. The inner cover 242 can be engaged or disengaged with respect to the case body 21 by turning a portable lock 243 disposed in an appropriate position on the top surface of the case body 21. The bottom surface of the cooling compartment 24 and the inner surface of the inner cover 242 are respectively formed with porous element mounts 393, 394 as in the second embodiment and half members 81, 82 constituting a porous element 80 are installed within these respective porous element bases 393, 394. Moreover, a nozzle socket 244 is disposed in an appropriate position of said inner cover 242.

To use this portable chiller, the cover 22 of the chiller case 20 is opened and the lock 243 is turned to release the inner cover 242 of the cooling compartment 24. Then, the inner cover 242 is opened and the eyedrop container 70 is taken out from the compartment 25 and loaded into the cooling compartment 24. There-after, the inner cover 242 is closed and the lock 243 is turned to engage the inner cover 242 with the case body 21. Then, the cylinder 10 is taken out from the cylinder compartment 130 and its nozzle 11 is inserted into the nozzle socket 244 of the inner cover 242 and the body of the cylinder 10 is pressed toward the inner cover 242, whereupon the nozzle 11 is forced into the cylinder 10 and the refrigerant is accordingly ejected from the cylinder 10 into the porous element 80 within the cooling compartment 24 to chill the eyedrop container 70. After cooling of this chilling, the lock 243 is turned to release the inner cover 242, the inner cover 242 is then opened and the chilled eyedrop container 70 is taken out.

The remainder of the structure of this portable chiller is similar to that of the preceding embodiments.

EXAMPLE 7

Figure 29:
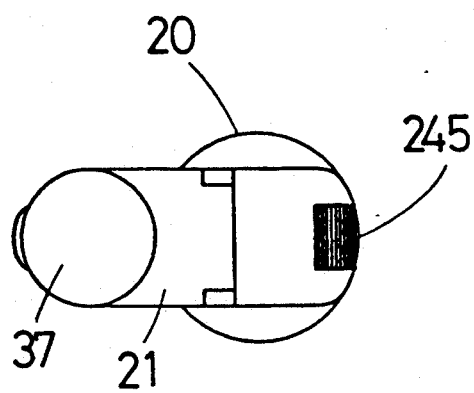
FIG. 29 is a plan view.
Figure 27:
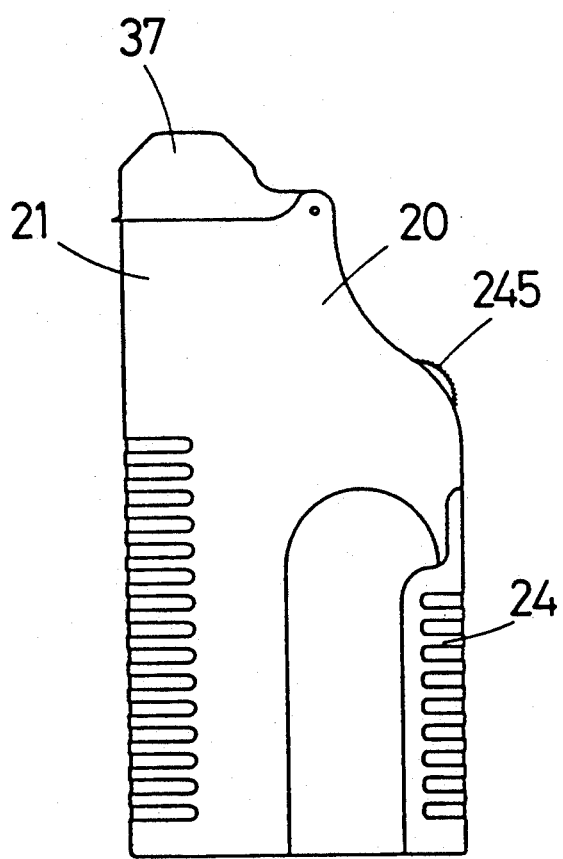
FIGS. 27 throuth 32 show a portable chiller as a seventh embodiment of the invention; wherein—
Figure 28:
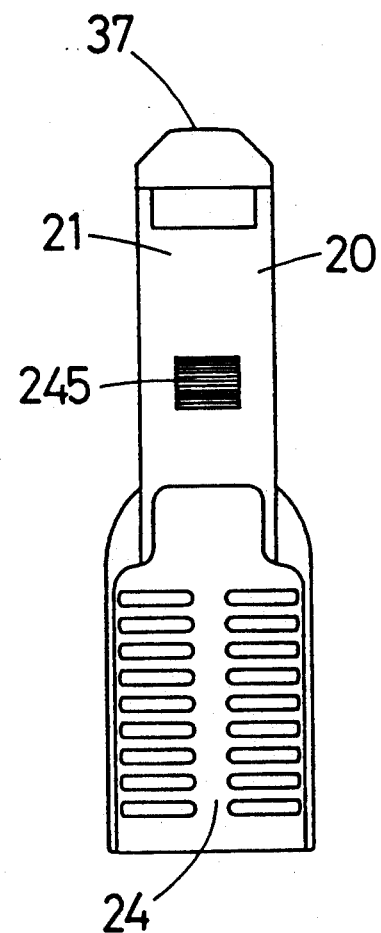
FIG. 28 is a left side elevation view.
Figure 30:
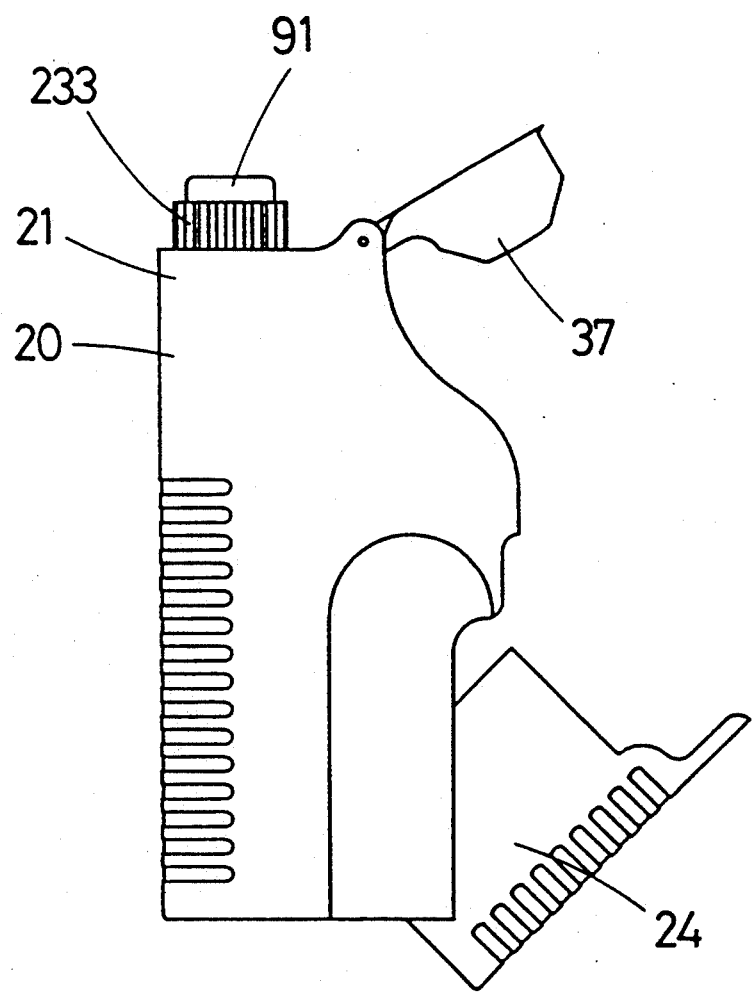
FIG. 30 is a front view showing a protective cap and a cooling compartment, both in opened condition.
Figure 31:
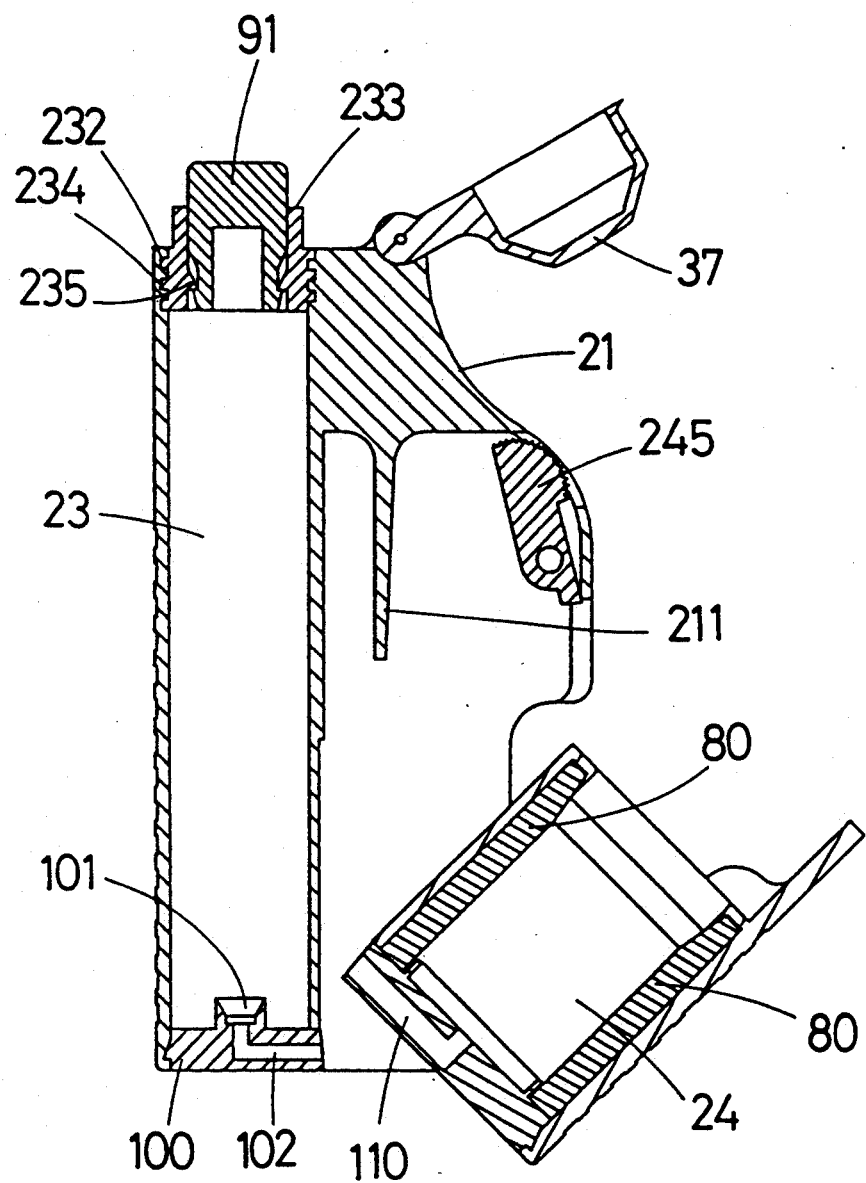
FIG. 31 is a longitudinal section view showing the same condition depicted in FIG. 30
Figure 32:
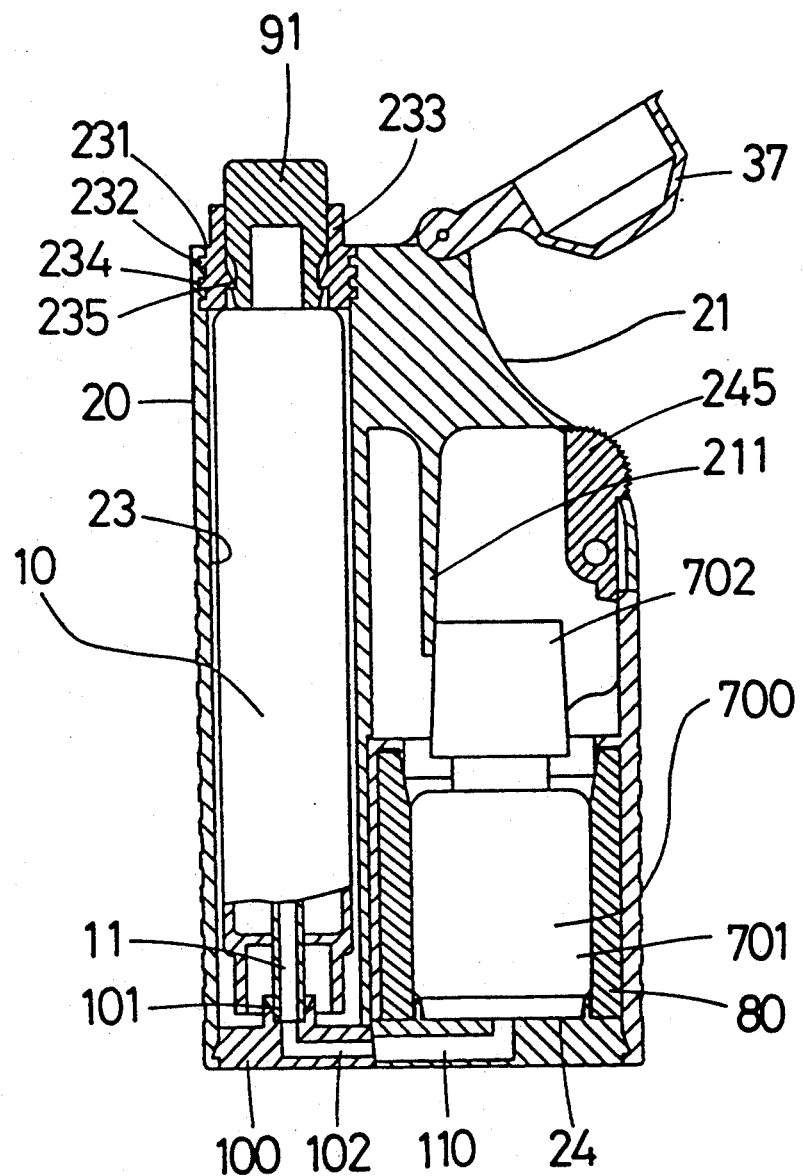
FIG. 32 is a longitudinal section view showing the cooling compartment loaded with an article to be chilled.

The seventh embodiment is illustrated in FIGS. 27 through 32. FIG. 27 is a front view; FIG. 28 is a left side elevation view, FIG. 29 is a plan view; FIG. 30 is a front view, with the protective cap 37 and cooling compartment 24 open; FIG. 31 is a longitudinal section view showing the chiller in the condition of FIG. 30; and FIG. 32 is a longitudinal section view showing the chiller loaded with the article 700 to be chilled in the cooling compartment 24. It should be understood that the like parts are indicated by the like numerals used for the preceding embodiments.

This embodiment is intended to be useful for situations where the article to be chilled is a smallsized bottle such as an ophthalmic drug bottle or a cosmetic bottle. This embodiment is distinct in that the whole cooling compartment is freely tiltable and the compartment for housing articles is omitted.

Thus, the top end of an ejection button 91 is projecting from the top of the chiller case 20 and a protective cap 37 adapted to cover said projecting end is attached rotatably to the top end portion of the case body 21.

The cooling compartment 24 is cup-shaped and is pivotally connected to the case body 21 in such a manner that it can tilt in and out about its lower end. This cooling compartment 24 has an inside diameter which is larger than the outer diameter of a barrel portion 701 of a bottle 700 to be chilled and a depth which is either equal to or slightly larger than said barrel 701. The inner peripheral surface of this cooling compartment 24 is thoroughly lined with a porous element 80. The thickness of this porous element 80 is slightly larger than the difference between the outer diameter of the barrel portion 701 of the bottle 700 and the inner diameter of the cooling compartment 24 so that when the cooling compartment 24 is loaded with the bottle 700, it closely contacts the peripheral surface of the barrel portion 701. Furthermore, a refrigerant passageway 110 disposed within the bottom wall of the cooling compartment 24 and a refrigerant passageway 102 within an adapter 100 disposed at the bottom of the cylinder compartment 23 are interconnected when the cooling compartment 24 as loaded into the case body 21.

The reference numeral 211 indicates a bottle locking member disposed within the case body 21. As the cooling compartment 24 carrying the bottle 700 is installed within the case body 21, this bottle 700 is installed within the case body 21, this bottle locking member 211 abuts against the lateral side of a cap 702 on the bottle 700 to prevent rattling of the bottle 700 and rising thereof from the cooling compartment 24.

The reference numeral 245 indicates a cooling compartment opening lever. As this lever 245 is pressed, the cooling compartment 24 is tilted out of the case body 21 to thereby open the cooling compartment 24.

To use this portable chiller, the cooling compartment opening lever 245 is pressed to open the cooling compartment 24 and after loading with the bottle 700 the cooling compartment 24 is pushed into the case body 21. As this is done, the cooling compartment opening lever 245 is reset in its original position.

Then, the protective cap 37 is opened to expose the ejection button 91, which is then depressed to deliver the refrigerant from the cylinder 10.

The ejected refrigerant enters into the cooling compartment 24 through the refrigerant passageway 102 within the adapter 100 and the refrigerant passageway 110 on the side of the cooling compartment 24.

As the refrigerant enters into the cooling compartment 24, a portion thereof is gasified but most of it retains its liquid form and flows through the clearance between the bottom surface of the cooling compartment 24 and the bottom surface of the bottle 700 into the porous element 80. The refrigerant absorbed into the porous element 80 diffuses throughout the porous element 80 under the pressure of ejection and by capillary action within the porous element 80 to remove heat from the porous element 80 and the air present therein. As a consequence, the whole porous element 80 is chilled and the barrel portion 701 of bottle 700 enshrouded by the porous element 80 is chilled from its entire peripheral surface.

After waiting for complete chilling, the cooling compartment 24 is opened by manipulating the cooling compartment opening lever 245 and the chilled bottle 700 is taken out for serving.

While the article to be chilled is an eyedrop container-dispenser, an eye drop bottle or a cosmetic bottle in the above embodiments, the article is not limited to these but may be a container containing any other drug, cosmetic or even a beverage. Moreover, the shape and size of the portable chiller according to the present invention are chosen appropriately according to the kind of the article to be chilled.

What is claim is:

1. A portable chiller comprising a cylinder means having a cylinder body containing a liquefied gas refrigerant and a nozzle for ejecting said refrigerant from said cylinder body only when it is forced into said body and a chiller case, said chiller case including:
   a cylinder compartment for accommodating said cylinder,
   a cooling compartment which is loaded with a replaceable article to be chilled and in which said article is chilled,
   a refrigerant ejection means for ejecting the refrigerant from said cylinder in said cylinder compartment into said cooling compartment, and
   a refrigerant gasification control means for allowing the refrigerant ejected into said cooling compartment to first circulate in liquid form around the article to be chilled in said cooling compartment and, then, be gasified, wherein said refrigerant gasification control means is resilient and substantially surrounds and directly contacts the peripheral surface of said replaceable article, wherein a portion of said replaceable article and a portion of said cooling compartment has a clearance therebetween for receiving therein said refrigerant gasification control means, and wherein another portion of said replaceable article and another portion of said cooling compartment has another clearance therebetween for receiving therein said refrigerant and for transferring said refrigerant into said refrigerant gasification control means.

2. A portable chiller according to claim 1 wherein said refrigerant gasification control means is a porous element enshrouding an article to be chilled in said cooling compartment and adapted to absorb the refrigerant ejected from said cylinder in liquid form and allow it to be gasified evenly around said article.

3. A portable chiller according to claim 2 wherein said porous element is made of sponge.

4. A portable chiller according to claim 2 wherein said porous element is made of nonwoven fabric.

5. A portable chiller according to claim 2 wherein said porous element is made of paper.

6. A portable chiller according to claim 2 wherein said porous element is made of a synthetic rubber containing a multiplicity of air coils.

7. A portable chiller according to claim 2 wherein said porous element is made of a urethane resin containing a multiplicity of air cells.

8. A portable chiller according to claim 2 wherein said porous element is secured to said cooling compartment.

9. A portable chiller according to claim 2 wherein said porous element is previously fitted around the article to be chilled before the article is loaded into the cooling compartment and removable from the article after chilling.

10. A portable chiller comprising a cylinder having a cylinder body filled with a liquefied refrigerant gas and a nozzle adapted to eject said refrigerant from said cylinder body only when it is forced into the cylinder body and a chiller case, said chiller case including:
    a cylinder compartment in which said cylinder is accommodated,
    a cooling compartment having a nozzle socket for accepting said nozzle and being adapted to accommodate a replaceable article to be chilled for chilling of the same, and
    a refrigerant gasification control means for allowing the refrigerant ejected from the cylinder taken out from said cylinder compartment into said cooling compartment through said nozzle socket to circulate in liquid form around the article in said cooling compartment and then, be gasified in situ to chill said article, wherein said refrigerant gasification control means is resilient and substantially surrounds and directly contacts the peripheral surface of said replaceable article, wherein a portion of said replaceable article and a portion of said cooling compartment has a clearance therebetween for receiving therein said refrigerant gasification control means, and wherein another portion of said replaceable article and another portion of said cooling compartment has another clearance therebetween for receiving therein said refrigerant and for transferring said refrigerant into said refrigerant gasification control means.

* * * * *